United States Patent
Kohn et al.

(10) Patent No.: US 6,517,824 B1
(45) Date of Patent: *Feb. 11, 2003

(54) POLYMER COMPOSITIONS COMPRISING ANTIFIBROTIC AGENTS, AND METHODS OF TREATMENT, PHARMACEUTICAL COMPOSITIONS, AND METHODS OF PREPARATION THEREFOR

(75) Inventors: Joachim Kohn, Highland Park, NJ (US); John E. Kemnitzer, III, Plainsboro, NJ (US); George J. Poiani, Jamesburg, NJ (US); David J. Riley, New Brunswick, NJ (US)

(73) Assignees: University of Medicine & Denistry of New Jersey, New Brunswick, NJ (US); Rutgers University, New Brunswick, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/650,324

(22) Filed: May 20, 1996

Related U.S. Application Data

(63) Continuation-in-part of application No. 08/479,150, filed on Jun. 7, 1995, now Pat. No. 5,660,822, which is a division of application No. 08/260,080, filed on Jun. 15, 1994, now Pat. No. 5,720,950, which is a division of application No. 07/934,818, filed on Aug. 24, 1992, now Pat. No. 5,372,807, which is a continuation of application No. 07/523,232, filed on May 17, 1990, now abandoned, said application No. 08/260,080, is a continuation of application No. 07/726,301, filed on Jul. 5, 1991, now Pat. No. 5,219,564, which is a continuation of application No. 07/549,494, filed on Jul. 6, 1990, now abandoned.

(51) Int. Cl.$^7$ ............ A61K 31/74; A61K 47/48

(52) U.S. Cl. ............... 424/78.06; 424/78.17; 424/78.08; 424/78.27

(58) Field of Search ............ 424/78.27, 78.17, 424/78.08, 78.66

(56) References Cited

U.S. PATENT DOCUMENTS 4,428,939 A   1/1984   Prockop (List continued on next page.)

FOREIGN PATENT DOCUMENTS

| EP | 0040506 | * 11/1981 |
| EP | 0 080 822 | 11/1982 |

OTHER PUBLICATIONS

"Conjugates of CIS–Y–Hydroxy–L–Proline . . . in vivo" Bioconjugate Chemistry Sep. 1994, 5. G. J. Poiani et al.*

(List continued on next page.)

*Primary Examiner*—Thurman K. Page
*Assistant Examiner*—T. Ware
(74) *Attorney, Agent, or Firm*—Perkins Coie

(57) ABSTRACT

A method for treating pulmonary hypertension and other diseases involving a defect in collagen metabolism, by administration of an effective amount of a liposome encapsulated copolymer conjugate antifibrotic composition, is disclosed. The antifibrotic agent is preferably a proline analog, such as cis-4-hydroxy-L-proline (cHyp). Consistent, high loadings (>98%) of the antifibrotic agent are achieved by first forming a dipeptide with L-lysine, after which the dipeptide is copolymerized with the polymer component to form the copolymer conjugate. The polymer is preferably poly(ethylene glycol) having a weight average molecular weight of from about 500 to about 15,000. There is thus provided the efficient delivery and rateable release of the antifibrotic agent to inhibit collagen accumulation and thereby treat the diseases involved. Accordingly, there is a substantial reduction in the quantity of antifibrotic agent necessary, and thus a corresponding reduction in the potential for toxicity that would otherwise result from its prolonged administration.

5 Claims, 17 Drawing Sheets

U.S. PATENT DOCUMENTS

| | | | |
|---|---|---|---|
| 4,672,031 A | | 6/1987 | Prockop |
| 4,755,379 A | * | 7/1988 | Jozefonvicz et al. ...... 424/78.29 |
| 4,906,476 A | | 3/1990 | Radhakrishnan |
| 5,219,564 A | | 6/1993 | Zalipsky |
| 5,372,807 A | * | 12/1994 | Poiani et al. ............ 424/78.36 |
| 5,455,027 A | | 10/1995 | Zalipsky et al. |
| 5,660,822 A | * | 8/1997 | Poiani et al. ............ 424/78.17 |
| 5,962,216 A | * | 10/1999 | Trouet et al. ............ 424/78.08 |

OTHER PUBLICATIONS

Abuchowski et al. "Alteration of immunological properties of bovine serum albumin by attachment of polyethylene glycol." J. Biol. Chem. 252 (11):3578–81. (1977).

Ajisaka et al. "Modification of human hemoglobin with polyethylene glycol: a new candidate for blood substitute." Biochem. Biophys. Res. Commun. 97 (3):1076–81. (1980).

Bowers–Nemia et al. (1983) Heterocycles 20:817–28.

Chen et al. (1966) J. Biol. Chem. 261:2599–604.

Ertel et al. "Copolymers of amino acids and poly(ethylene glycol): a new family of functionalized drug–carriers." Polym. Mat. Sci. Eng. 66: 486–7. Proc. Am. Chem. Soc. (1991).

Greco et al. (1994) Am. J. Respir. Crit. Care Med. 149:A185.

Greco et al. (1994) Am. J. Respir. Crit. Care Med. 149:A382.

Greco et al. (1995) Am. J. Respir.Crit. Care Med. 151:A63.

Greco et al. (1996) Am. J. Respir. Crit. Care Med. 153:A149.

Kohn et al. "Polymerization Reactions involving the side chains of alpha–L–amino acids." J. Am. Chem. Soc. 109: 817–20. (1987).

Nathan et al. "Polyethylene glycol—lysine copolymers: new biocompatible polymers for biomedical applications." J. Polym. Preprints 1990 31(2):213–14.

Ouchi et al. Synthesis of 5–fluorouracil–terminated monomethoxypoly(ethylene glycol)s, their hydrolysis behavior, and their antitumor activities. J. Macromol. Sci.–Chem. A24(9): 1011–32. (1987).

Papaioannou et al. (1990) Acta Chemica Scandinavica 44:243–51.

Poiani, Kemnitzer, et al. (1995) Am. J. Respir. Crit. Care Med. 151:A734.

Poiani, Fox, et al. (1995) Am. J. Respir. Crit. Care Med. 151:A734.

Poiani et al. (1995) Amino Acids 9:237–48.

Poiani et al. (1994) Am. J. Respir. Crit. Care Med. 150:1623–7.

Poiani et al. (1995) Bioconjugate Chem. 5:621–30.

Poiani et al. "Intermittent intravenous delivery of antifibrotic agent in liposomes reduces the dose required to prevent hypoxic pulmonary hypertension in the rat." Am. Rev. Resp. Dis. 141: A186 (1990) (abstract).

Poiani et al. "Local delivery of liposome–encapsulated proline analogue prevents pulmonary hypertension in the rat." in Amino Acids: Chemistry, Biology and Medicine. Lubec, G. and Rosenthal, eds. pp. 634–642. (1990) (same as Chem. Abstracts 115(16): 166492e.

Poiani et al. An antifibrotic agent reduces blood pressure in established pulmonary hypertension in the rat. J. Appl. Physiol. 68: 1542–47. (1990).

Poiani et al. "Liposome–encapsulated antifibrotic agent prevents early hypoxic pulmonary hypertension in the rat." Am. Rev. Resp. Dis. 139:A172. (1989) (abstract).

Prockop. "Regulation of the collagen synthesis in animal cells by Proline and lysine analogs". Chem. Abstracts 78(10): 250, 62201k. (1973).

Prockop. Controlling cellular synthesis of collagen with cis–L–proline and/or L–lysine derivatives. Chem. Abstracts 79(14):326, 83465k. (1973).

Riley et al. (1984) "Effect of proline analogs on oxygen toxicity–induced pulmonary fibrosis in the rat." Chem. Abstracts 101(23): 43, 204139r.

Zalipsky et al. "Succinimidyl carbonates of polyethylene glycol: useful reactive polymers for poreparation of protein conjugates." in Polymeric Drugs and Drug Delivery Systems. Dunn et al., ed. Am. Chem. Soc. 469:91–100. (1991).

Zalipsky et al. "Attachment of drugs to polyethylene glycols." Eur. Polym. J. 19(12): 1177–83. (1983).

* cited by examiner

Scheme 1: Step a

Poly(PEG-Lys-cHyp amide)

IV

Scheme 1: Step b

POLYMER COMPOSITIONS COMPRISING ANTIFIBROTIC AGENTS, AND METHODS OF TREATMENT, PHARMACEUTICAL COMPOSITIONS, AND METHODS OF PREPARATION THEREFOR

CROSS-REFERENCE TO RELATED APPLICATIONS

This application is a continuation-in-part of application Ser. No. 08/479,150 filed Jun. 7, 1995, now U.S. Pat No. 5,660,822; which is a divisional application of application Ser. No. 08/260,080 filed Jun. 15, 1994, now U.S. Pat. No. 5,720,950; which is (1) a division of 07/934,818, filed Aug. 24, 1992, now U.S. Pat. No. 5,372,807, which is a continuation-in-part of application Ser. No. 07/864,361 filed on Apr. 6, 1992 which is a continuation of application Ser. No. 07/523,232 filed on May 14, 1990, now abandoned; and which is also (2) a continuation in part of application Ser. No. 07/726,301 filed Jul. 5, 1991, now U.S. Pat. No. 5,219,564; which is a continuation of application Ser. No. 07/549,494 filed on Jul. 6, 1990, now abandoned. All of the above-enumerated applications are incorporated herein by reference, each in its entirety.

FIELD OF THE INVENTION

The present invention relates generally to the treatment of fibrotic conditions, and to the use of antifibrotic agents for the amelioration and modification of such diseases. The present invention is also concerned with therapeutic compositions in which antifibrotic agents are chemically combined with carriers such as polymers in order to enhance the pharmacokinetic profile of the antifibrotic agents.

BACKGROUND OF THE INVENTION

The fibrotic conditions which the present invention is intended to treat include changes in the structure and function of various organs in connection with the metabolism of collagen and other biomolecules. One of the long-term sequelae of hypertension is the deposition of connective tissue in walls of blood vessels. In hypertensive rats, collagen biosynthesis and deposition are increased in the aorta, and these effects are reversed when blood pressure is lowered by antihypertensive drugs. Treatment of animals with experimental hypertension with agents that selectively inhibit collagen formation and reduce vascular collagen content, suggesting that increased collagen contributes to the maintenance of hypertension. Although the use of antifibrotic agents has increased the understanding of the role of collagen in hypertension and vascular disease, their application as potential therapeutic agents for chronic conditions has been limited.

Collagen is the most abundant protein in vertebrates. The biosynthesis of collagen involves unique post-translational modification of pro-alpha chains. Hydroxylation of prolyl and lysyl residues, a key part of collagen formation, is vital for normal triple-helix formation and intermolecular cross-linking. When post-translational processing is inhibited, non-helical procollagen forms, and it is then degraded by intracellular proteases and is secreted into the extracellular matrix at a slower rate as a nonfunctional protein. The incorporation of proline analogues, e.g., cis-4-hydroxy-L-proline (cHyp), into nascent pro-alpha chains reduces the extracellular accumulation of collagen. The agents described herein are believed to act more generally by inhibiting collagen synthesis and thereby averting certain of the pathophysiological sequelae of fibrosis, such as atherosclerosis and hypertension. Through the distortion of bond angles and from steric hindrance among polypeptide chains; cHyp inhibits the folding of pro-alpha chains into a stable triple helix. Other proline analogues such as cis-4-fluoroproline, cis-4-bromoproline, and 3,4-dehydroproline have similar effects, but can also inhibit other post-translational steps. The compound 3,4-dehydroproline is an example of a proline analogue which can also inhibit other post-translational steps; for example, 3,4-dehydroproline inhibits prolyl hydroxylase activity. This proline analogue has been administered to humans with pulmonary fibrosis in the condition referred to as adult respiratory distress.

The antifibrotic agents described herein are most effective in tissues undergoing rapid rates of collagen synthesis. For example, collagen comprises about one-third of the dry weight of pulmonary arteries in which synthesis increases rapidly following induction of hypertension. Exposure to hypoxia causes constriction of small pulmonary arteries and hypertension develops form sustained vasoconstriction and structural changes in the vascular wall. Proliferation of vascular smooth muscle cells and connective tissue accumulation thicken the vessel walls and narrow the lumen of pulmonary arteries. These structural changes cause or contribute to hypertension.

Collagen metabolism has been implicated as a negative factor in other diseases and conditions. For example, scar tissue is comprised largely of collagen. While some scar tissue is normal as a result of the closure and healing of wounds, excess scar tissue and collagen based adhesions are often undesirable and unhealthy. It is important to note, accordingly, that several proline analogues have been shown to be effective in inhibiting scar formation.

The present invention in particular relates to polymers which contain the antifibrotic compounds described herein, pharmaceutical compositions containing such polymers and various methods of preparation and use. In such polymers, cis-hydroxyproline (cHyp) or another antifibrotic agent is the pharmacologically active agent, useful in controlling the proliferation of collagen or the other changes in tissue as described herein in detail. This is particularly important in diseases and conditions where collagen is deposited or synthesized in abnormally high levels, or where collagen is not properly broken down or removed, contributing to the pathology of the particular disease or condition. In the past it has been recognized that cHyp is active in reducing the abnormal proliferation of collagen. More particularly, the pharmacological effectiveness of cHyp has been demonstrated in treating pulmonary fibrosis. Unfortunately, it is also recognized that cHyp can be potentially toxic if used improperly, particularly in chronic use, and thus has had limited clinical utility.

In recent efforts to provide a stable carrier for cHyp, poly tethylene glycol-co-lysine) (PEG-Lys) functioned as such a carrier for the antifibrotic agent; Poiani et al., *Bioconjugate Chemistry;* 1994; 5(6):621–630. It was demonstrated that a hydrolytically stable amide-linkage between cHyp and the polymeric backbone is needed to maximize the antifibrotic activity both in vitro and in vivo; Poiani, G. J., et al., supra. Typically, the cHyp is coupled to the free acid carrier via the dicyclohexylcarbodiimide, 4-dimethylaminopyridine (DCC/DMAP) system. However, the primary disadvantage of this system is the significant variability in cHyp attachment. The maximum degree of attachment via this coupling scheme for the amide-linked cHyp is approximately 65%, requiring a three-fold excess of the appropriately protected cHyp. In order to alleviate this variability and low degree of drug incorporation, the present invention uses the dipeptide of L-Lys and cHyp as the drug-containing chain extender. Thus, controlled dosage forms, i.e., mg/ml of a carrier matrix for which a specific drug content is maintained, can be readily obtained and administered.

The present invention thus provides an improved synthetic scheme that has been developed in order to optimize the capacity of cHyp that can be conjugated to the poly (PEG-Lys) carrier, and a detailed hydrolytic stability profile has been developed. In a further extension of the present invention, aimed at combining the high bioactivity of poly (PEG-Lys-cHyp) which has been observed with further extensions of existing treatments into fibrotic lung disorders, there is also provided intravenous liposomal delivery of drug conjugates using non-immunogenic polysaccharide-coated vesicles. Organ distribution and biological stability were investigated using radiolabeled drug conjugates of the present invention.

The controlled release and targeting of drugs to specific cells and organs has become increasingly important. Accordingly, the present invention provides a hybrid drug delivery system comprising a non-specific, non-cytotoxic, polymeric carrier containing a covalently bound, low molecular weight, water soluble, polar drug delivered by means of a liposomal vehicle containing target-specific ligands. Data has been gathered and is presented below in order to demonstrate the efficacy of this drug delivery system, as well as to illuminate the general principles on which it operates. The targeting of such sustained release antifibrotic treatment compositions to tissues with increased collagen production is an approach which can be taken in order to prevent organ fibrosis. Broader applications are found in treating scar for mnation, adhesions, and fibrosing disorders of other visceral organs.

Accordingly, the present invention seeks to overcome the disadvantages of past approaches to treatment of fibrotic diseases. Thus, one object of the present invention is to facilitate the use of antifibrotic agents in the treatment of diseases and conditions in which collagen metabolism is to be modified, such as when excess collagen synthesis or deposition occurs.

Another object of the present invention is to combine the antifibrotic agents described herein with other compounds, e.g., polymers, to improve the pharmacokinetic profile of these drugs.

Another object of the present invention is to combine the therapeutic agents with compounds which have little if any toxicity or side effects of their own.

Another object of the present invention is to enhance the delivery of the antifibrotic agents to the site of activity.

Another object of the present invention is to provide antifibrotic agents in a variety of polymeric and monomeric forms which can be used to modify the pharmacokinetic profile of the agent in question.

These and other objects will be apparent to those of ordinary skill in the art from the teachings which follow.

BRIEF DESCRIPTION OF THE PRIOR ART

The publications enumerated further below are illustrative of the state of the art which encompasses the above-defined field of the invention. Each said publication is hereby incorporated herein by reference, each in its entirety:
Abuchowski et al., *J. Biol. Chem.,* 1977, 252(11):3578;
Ajisaka et al., *Biochem. Biophys. Res. Commun.,* 1980, 97(3):1076;
Bowers-Nemia et al., *Heterocycles,* 1983, 20(5):817;
Zalipsly et al., *Eur. Polym. J.,* 1983, 19 (12):1177;
Kohn et al., *J. Am. Chem. Soc.,* 1987, 109:817;
Ouchi et al., *J. Macromol. Sci.—Chem.,* 1987, A24(9):1011;
Yamsuki et al., *Agric. Biol. Chem.,* 1988, 52:2185–2196;
Nathan et al., *J. Polym. Preprints* 1990, 1990, 31(2):213;
Papaioannu et al., *Acta Chem. Scand.,* 1990, 44:243;
Poiani et al., *Amino Acids: Chem. Biol. & Med.,* Lubec and Rosenthal, eds., 1990, 634–642;
Poiani et al., *J. Appl. Physiol.,* 1990, 68:1542;
Somak et al., *Free Rad. Res. Commun.,* 1991, 12–13:553–562;
Zalipsky et al., "In Polymeric Drugs and Drug Delivery Systems", Dunn and Ottenbrite, eds., *Am. Chem. Soc.,* 1991, 469:91;
Ertel et al. In *Polym. Mat. Sci. Eng. American Chem. Soc.,* 1992, 66:486;
Nathan et al., *Macromolecules,* 1992, 25:4476–4484;
Roseng, et al., *J. Biol. Chem.,* 1992, 267(32):22981–22993;
Nathan et al., *Bioconjugate Chem.,* 1993, 4:54–
Nathan et al., *J. Bioact. Compat. Polym.,* 1994, (in press);
Poiani et al., *Bioconjugate Chem.,* 1994, 5(6):621–630;
Monfardini et al., *Bioconjugate Chem.,* 1995, 6:62–69;
Zalipsky, *Bioconjugate Chem.,* 1995, 6(2):150–165;

SUMMARY OF THE INVENTION

In accordance with the present invention, an antifibrotic composition is disclosed which comprises one or more dipeptides consisting of an L-proline or derivative antifibrotic agent comprising one or more members selected from the group consisting essentially of 3,4-dehydro-L-proline and laevo and cis isomers of compounds of the general structural formula:

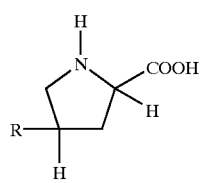

(I)

wherein R is OH, Cl, F, $NH_2$, SH, $SCH_3$, $OCH_3$, $ONO_2$, $OSO_2$, $OSO_3H$, $H_2PO_4$, or COOH; and pharmaceutically acceptable salts thereof; said L-proline or derivative antifibrotic agent being covalently bound to L-lysine to form each dipeptide, which in turn is covalently bound to a polymer comprising one or more monomers or prepolymers selected from the group consisting essentially of ethylene glycol, propylene glycol, butylene glycol, isobutylene glycol, and povidone to form a copolymer conjugate; wherein said antifibrotic composition is prepared by covalently binding said L-proline or derivative antifibrotic agent to said L-lysine to form one or more said dipeptides, and thereafter covalently binding said dipeptide to said polymer to form said copolymer conjugate, wherein said formation of said copolymer conjugate proceeds to give in excess of a 98% yield.

In particular, the present invention provides an antifibrotic composition wherein the L-proline or derivative antifibrotic agent is cis-4-hydroxyproline, and the polymer is poly (ethylene glycol) having a weight average molecular weight of from about 500 to about 15,000.

The present invention also provides intermediates useful in the process of making the copolymer conjugates. These intermediates comprise the dipeptides consisting of an L-proline or derivative antifibrotic agent as defined above, covalently bound to L-lysine to form each dipeptide. Said intermediates have the following formula:

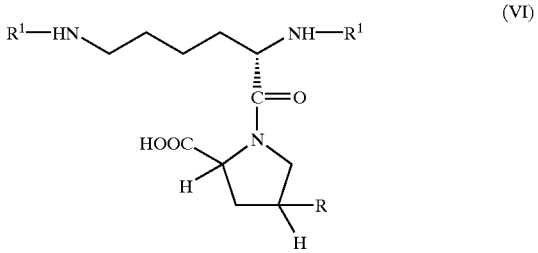

(VI)

wherein $R^1$ is a conventional amine protecting group; and R is OH, Cl, F, $NH_2$, SH, $SCH_3$, $OCH_3$, $ONO_2$, $OSO_2$, $OSO_3H$, $H_2PO_4$, or COOH; and pharmaceutically acceptable salts thereof.

There is further provided a method of preparing the antifibrotic composition described above, comprising covalently binding said L-proline or derivative antifibrotic agent to said L-lysine to form one or more said dipeptides, and thereafter covalently binding said dipeptide to said polymer to form a copolymer conjugate, under conditions which do not substantially reduce the pharmacological activity of the antifibrotic agent, and wherein said formation of said polymer conjugate proceeds to give in excess of a 98% yield. In particular, the Nα- and Nε-termini of the L-lysine are protected, e.g., with t-butoxycarbonyl, or other suitable amine protecting groups; and the N-hydroxysuccinimide ester of the L-lysine is used in the coupling reaction, along with conventional coupling agents, e.g., dicyclohexylcarbodiimide (DCC) together with dimethylaminopyridine (DMAP). After formation of the dipeptide, one or more thereof are then covalently bound to said polymer comprising one or more monomers or prepolymers selected from the group consisting essentially of ethylene glycol, propylene glycol, butylene glycol, isobutylene glycol, and povidone to form said copolymer conjugate. In this coupling reaction, the terminal hydroxyl groups of, e.g., poly(ethylene glycol), are activated with conventional activating groups, e.g., succinimide to form the bis(succinimidyl)carbonate of the polymer. Amide linkages are then formed between the dipeptide units and the polymer units by using conventional polymerization promoters, e.g., sodium bicarbonate.

The copolymer conjugates described above can be included in a pharmaceutical composition in combination with a pharmaceutically acceptable carrier. The pharmaceutically acceptable carrier may be any of those commonly recognized vehicles used in the formulation of pharmaceutical products.

Another aspect of the invention involves a pharmaceutical composition as described above, wherein the copolymer conjugate is used in, and as a part of, the pharmaceutically acceptable carrier, and thus serves as a carrier molecule for delivery of the antifibrotic active agent, while at the same time serving as a component of the delivery vehicle. Furthermore, the vehicle itself has a site specific makeup recognized by receptors in various organ tissues where the antifibrotic agents will be effective. A preferred embodiment of this dual use is a liposomal vehicle, e.g., PEG-conjugated liposomes, and additionally, liposomes coated with cholesterol derivatized amylopectin, wherein the antifibrotic copolymer conjugate is entrapped within said liposomes.

The invention also encompasses a method of treatment of diseases or conditions wherein abnormal collagen accumulation or proliferation is of concern, comprising administering to a mammalian patient in need of such treatment at least one of the antifibrotic agents described herein as a copolymer conjugate in an amount effective for treating the abnormality in collagen accumulation.

The diseases and conditions in which the antifibrotic agents described herein are particularly useful include pulmonary conditions, such as pulmonary fibrosis; atherosclerotic conditions, such as arteriosclerosis; renal disorders, such as renal hypertension; hepatic disorders, such as cirrhosis; scar formation, adhesions, and fibrosing disorders of other visceral organs; and other like conditions.

BRIEF DESCRIPTION OF THE DRAWINGS

The invention is further described and illustrated by means of the following drawings, in which:

FIG. 10 is a depiction of the synthetic scheme for the preparation of the L-lysine-cis-4-hydroxy-L-proline dipeptide (Lys-cHyp 2HCl), and is also identified as Scheme 1: Step a.

DETAILED DESCRIPTION OF THE INVENTION

Figure 1A:
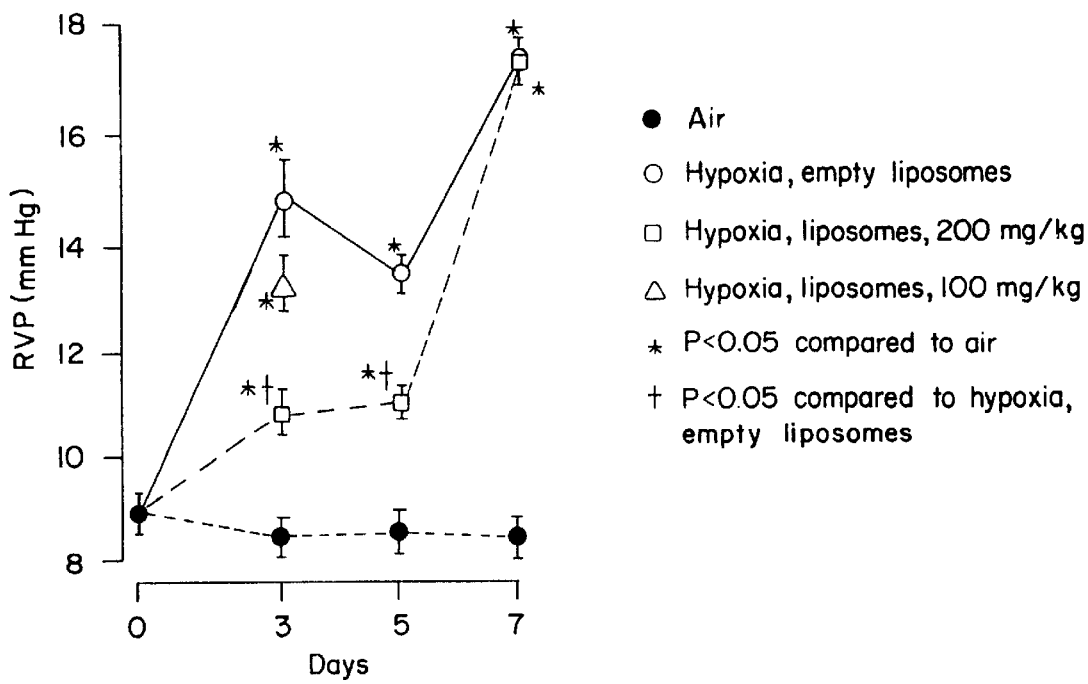
FIG. 1 is a graph depicting the effect of single intravenous injections of cHyp entrapped in liposomes on rats exposed to hypoxia (10% $O_2$) for 7 (C) Hematocrit. (D) Hydroxyproline content per vessel. (E) Protein content per vessel. Days indicate days of exposure to air. Data points, mean; bracket, ±SE, n=6–9 for each data point.
Figure 1B:
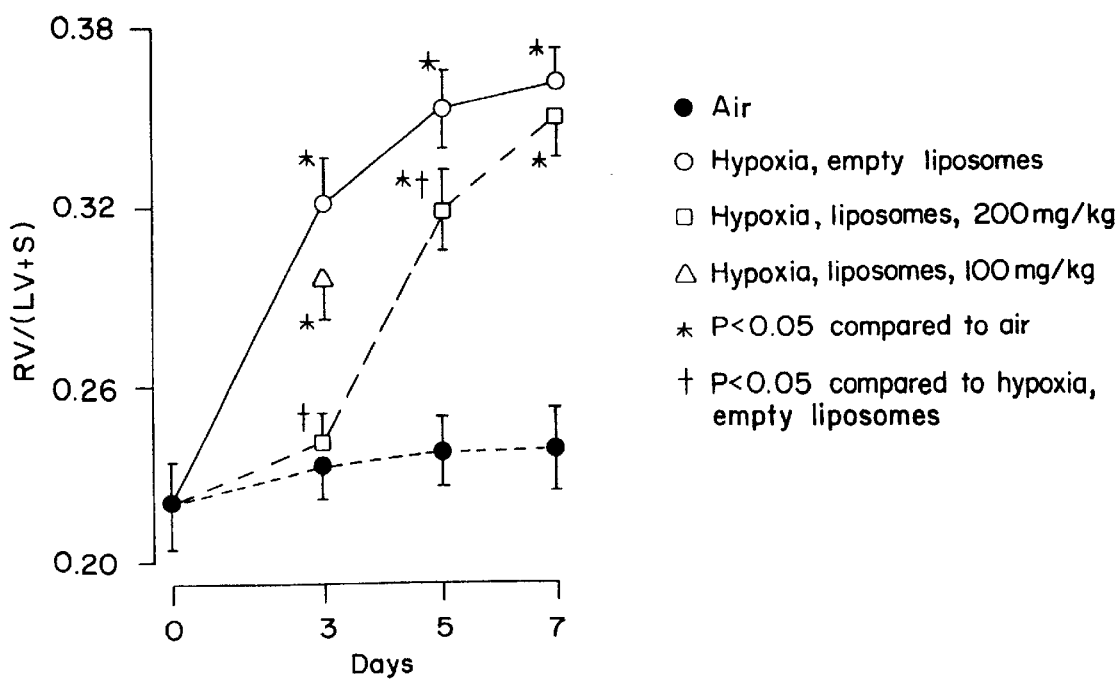
Figure 1C:
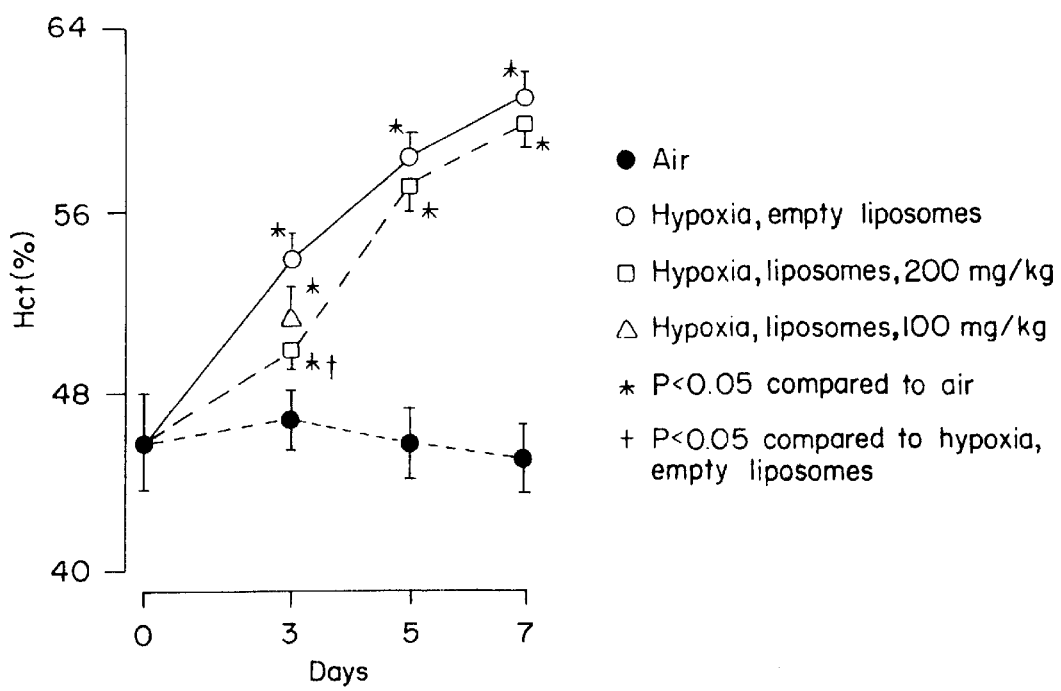
Figure 1D:
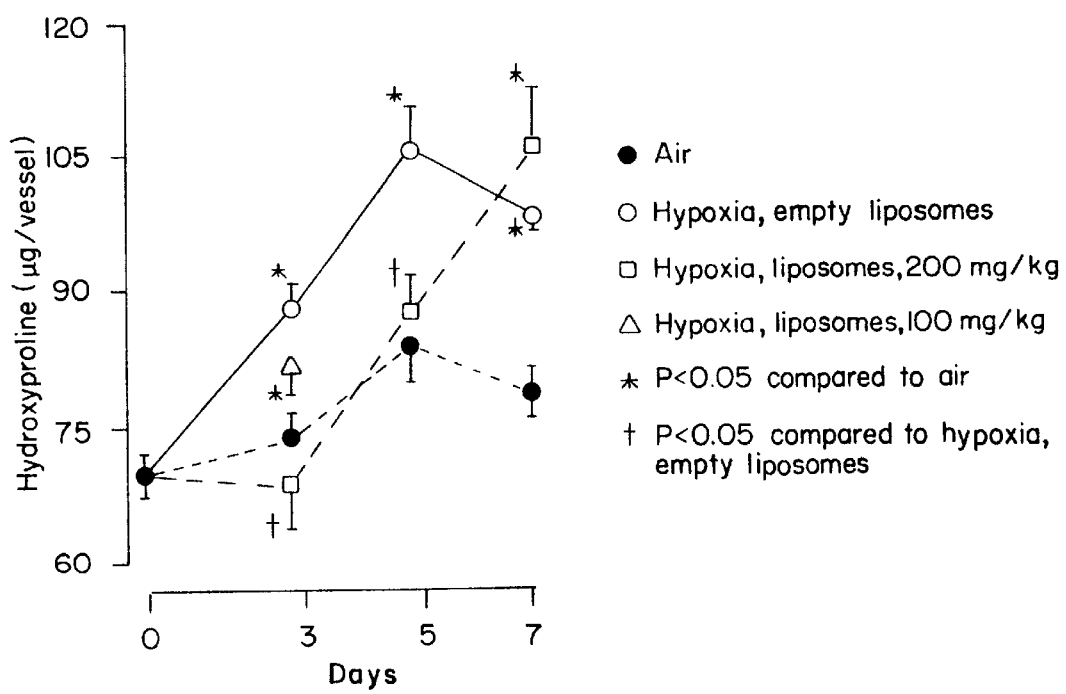
Figure 1E:
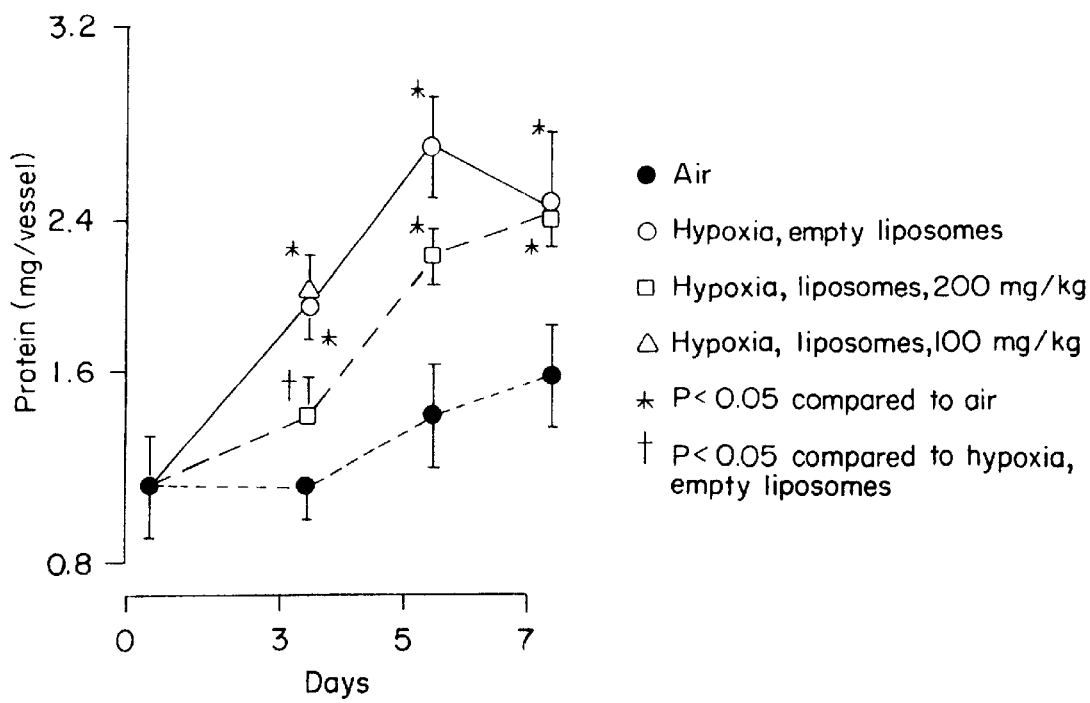
Figure 2A:
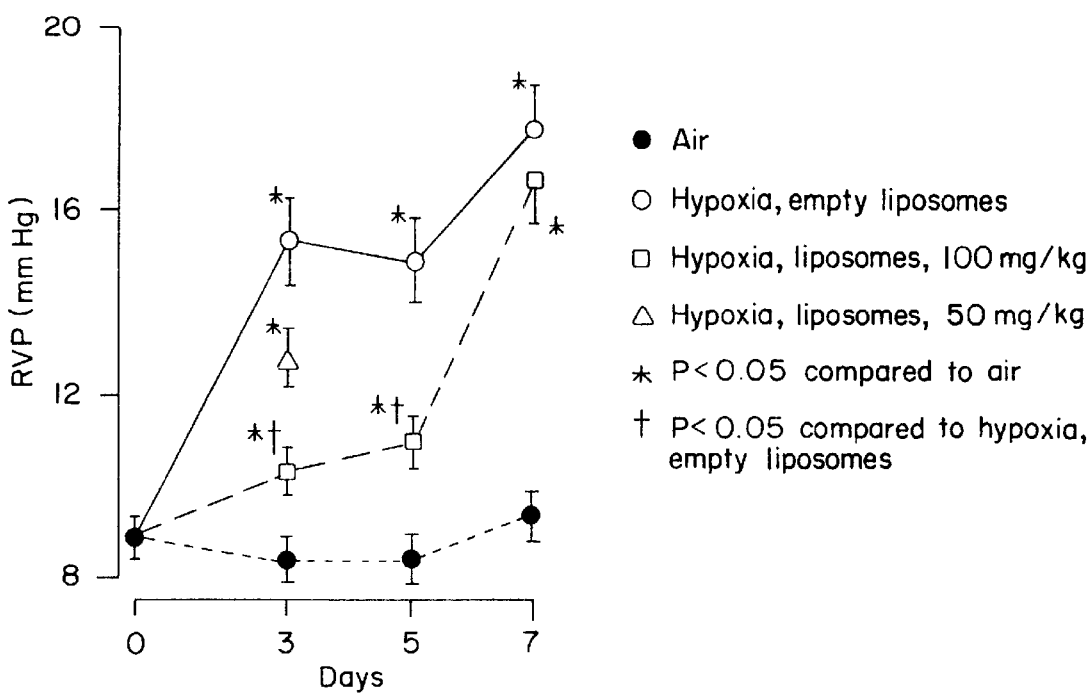
FIG. 2 is a graph depicting the effect of reticuloendothelial blockade with empty liposomes prior to intravenous injection of cHyp entrapped in liposomes on rats exposed to hypoxia (10% $O_2$) for 7 days. Format similar to FIG. 1. n=6–9 for each data point.
Figure 2B:
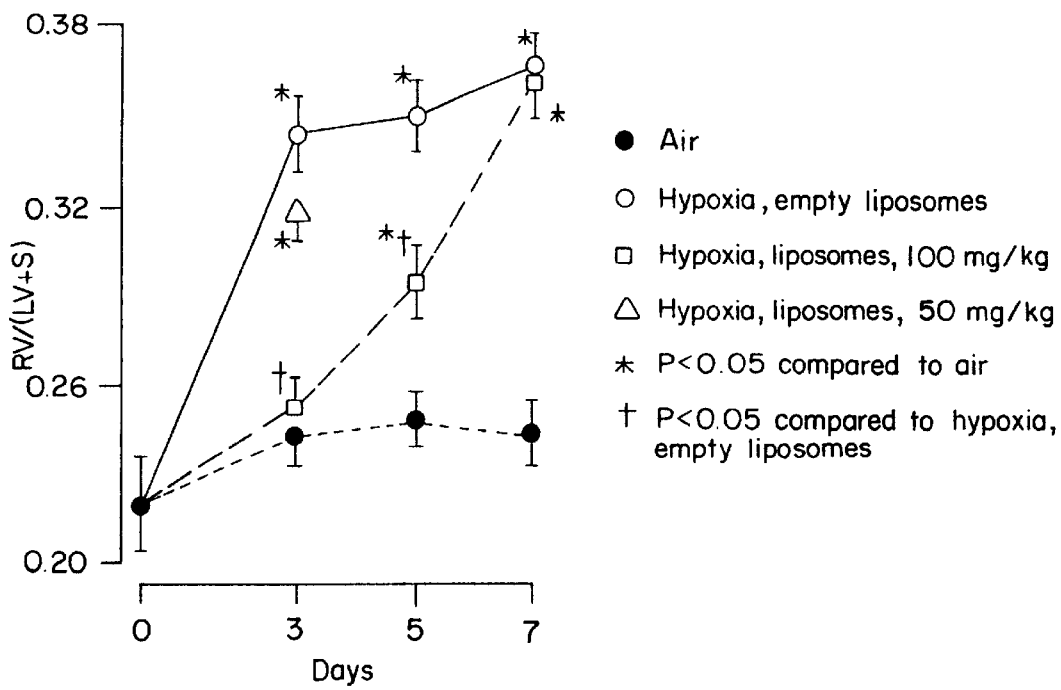
Figure 2C:
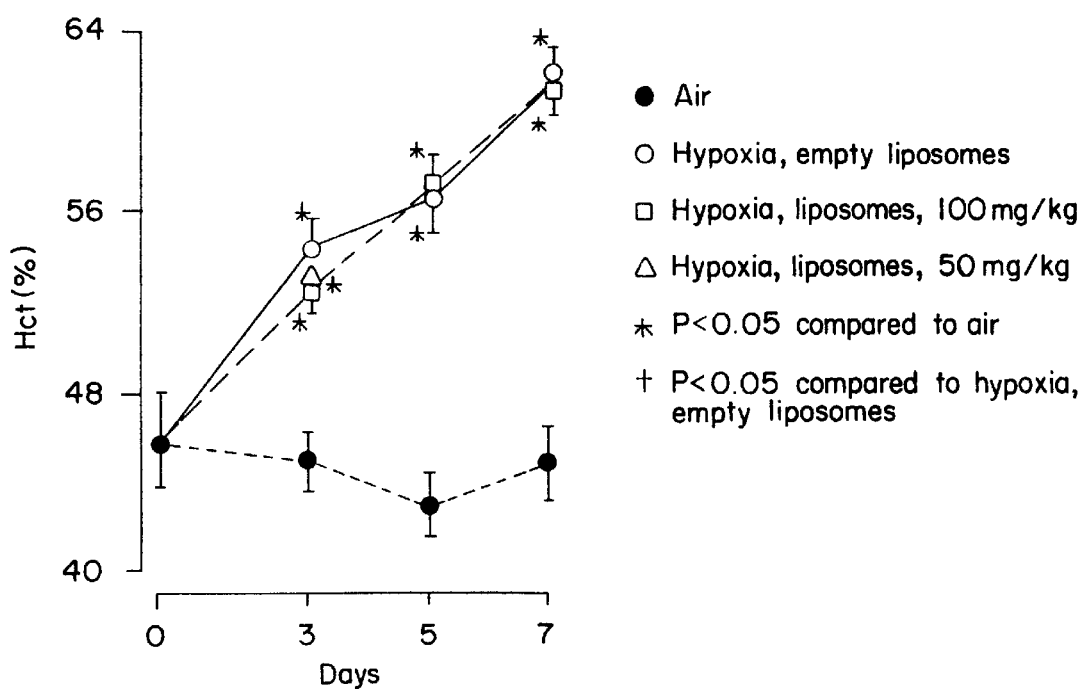
Figure 2D:
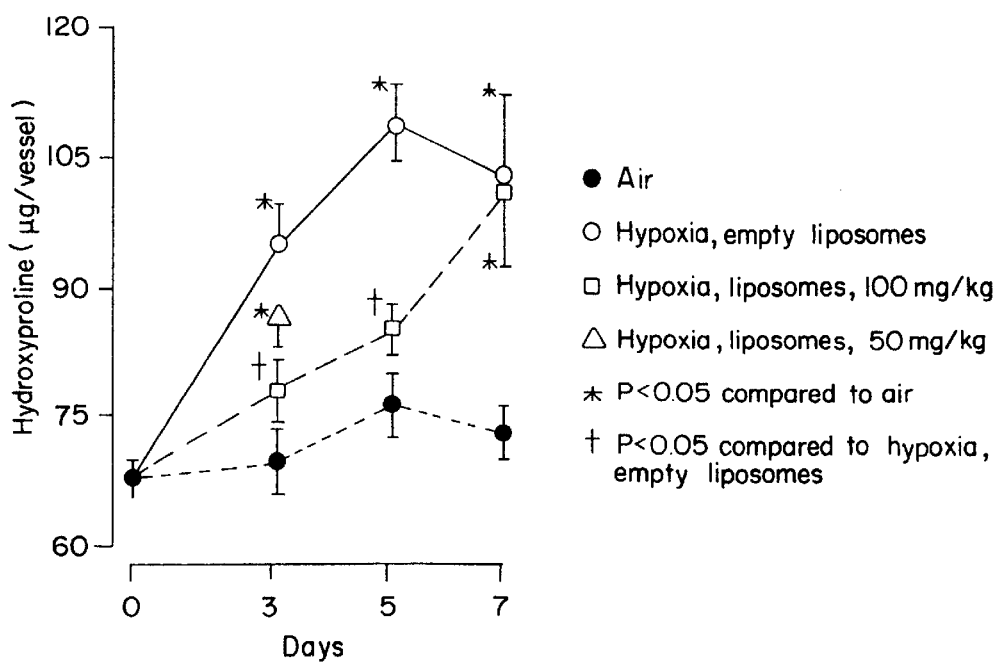
Figure 2E:
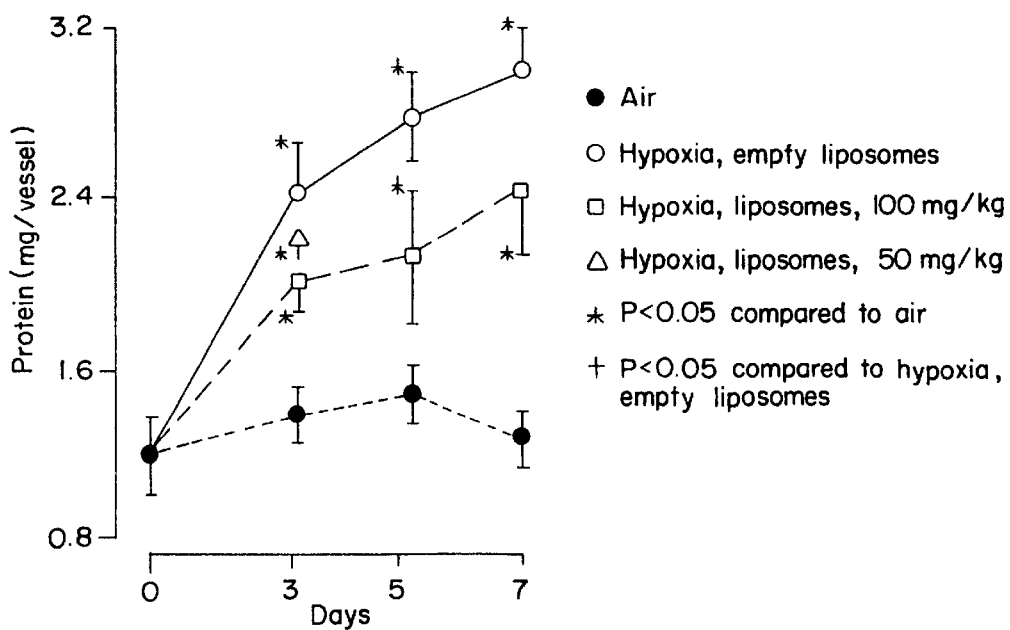

The description contained herein includes numerous terms which are well understood by those of ordinary skill in this art. In particular, however, the following terms used herein are intended to have the below-related meanings.

The term "antifibrotic agent" refers to chemical compounds which have antifibrotic activity in mammals. This takes into account the abnormal formation of fibrous connective tissue, which is typically comprised of collagen to a greater or lesser degree. These compounds may have different mechanisms of action, some reducing the formation of collagen or another protein, others enhancing the metabolism or removal of collagen in the affected area of the body. All such compounds having activity in the reduction of the presence of fibrous tissue are included herein, without regard to the particular mechanism of action by which each such drug functions.

It is recognized that certain drugs have been used in the treatment of diseases or conditions which typically accompany fibrotic changes in tissue, such as in the lungs. These overall conditions may be the subject of distinct treatment modalities for sequelae other than the fibrotic changes which are described herein. For example, in the patient with pulmonary fibrosis and pulmonary hypertension, such patients may be treated for the fibrotic changes in the lungs, independently from other treatment which may be rendered for the hypertensive aspects of the overall disease.

The term "backbone" is used to describe the portion of the polymers described herein formed by the polymerization of monomeric units and which typically form the structural components of the polymeric compound. The backbone may have one or more side chains attached to it. Both the backbone and the side chains may have functional or reactive moieties or groups contained therein or attached thereto. Some polymers described herein include the antifibrotic agent in the backbone, and many of the polymers described herein contain the antifibrotic agent linking compound in the polymer backbone. In certain polymers, particularly branched polymers, there may be little or no difference structurally between the backbone and the side chains, and the distinction between the two may be less significant. In other polymers, there may be a great difference between these portions of the polymer in reactivity, structure and the biological properties attributable thereto.

The term "molecular weight" refers to both number average and weight average molecular weights when used to describe the polymers of the invention. When used to refer to monomers, the antifibrotic agent or the antifibrotic agent-linking compound, the term is used in the conventional sense.

The term "linking compound" is not limited to molecules per se, and refers to compounds, molecules and molecular fragments, e.g., peptides, which can react with the polymer, monomers and antifibrotic agents to attach the antifibrotic agents to the polymer or to incorporate the antifibrotic agents into the polymer. As such, the linking molecule includes compounds and the like with more than one reactive group, preferably two or three reactive groups.

The term "reactive group" refers to chemical moieties which are attached to the polymer or bonds in the polymer which participate in the chemical reaction between the components involved, e.g., the antifibrotic agent or the linking compound. Examples of reactive groups include without limitation hydroxyl, carboxyl, amine, amide, carbon-carbon double and triple bonds, epoxy groups, halogen or other leaving groups and the like.

The term "pharmaceutically acceptable carrier" refers to those components in the particular dosage form employed which are inert and are typically employed in the pharmaceutical arts to formulate a particular active compound. This may include without limitation solids or liquids and gases, used to formulate the particular pharmaceutical product. Examples of carriers include diluents, flavoring agents, solubilizers, lubricants, suspending agents, binders or tablet disintegrating agents, encapsulating materials, penetration enhancers, solvents, emollients, thickeners, dispersants, sustained release forms, such as matrices, transdermal delivery components, buffers, stabilizers, preservatives and the like. Each of these terms is understood by those of ordinary skill.

When desired, the compounds. and compositions of the invention may also utilize liposome technology to facilitate delivery of the medication to the desired site. The liposomes may or may not utilize the polymer described herein in the structure thereof. Hence, if the polymer forms part of the liposome, it may be considered part of the pharmaceutically acceptable carrier itself. If the liposome is comprised of components other than the polymer mentioned above which is linked to or contains the antifibrotic agent, the liposome for purposes of explanation would be considered part of the carrier and the polymer with the antifibrotic agent attached thereto would be treated as the active compound.

Liposomes have been used to locally deliver drugs in concentrated form. Liposomes have been used to deliver cHyp intravenously to rats in order to treat experimental pulmonary hypertension. The blood vessels in rats made hypertensive undergo thickening, due in part to accumulation of collagen. The thickening and stiffening of these blood vessels contribute to increased resistance to blood flow and ultimately to elevated blood pressure.

The antifibrotic agent is one or more members selected from the group consisting of 3,4-dehydro-L-proline and laevo and cis isomers of compounds of the general structural formula:

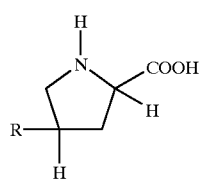

(I)

wherein R is OH, Cl, F, $NH_2$, SH, $SCH_3$, $OCH_3$, $ONO_2$, $OSO_2$, $OSO_3H$, $H_2PO_4$, or COOH; and pharmaceutically acceptable salts therefor.

The preferred antifibrotic compounds include cHYP and its analogs. The most preferred antifibrotic compound is cHYP.

The antifibrotic agents can be operatively linked to the polymer or incorporated into the polymer, in such a way as to effectuate release thereof over time as the polymer is metabolized. The expression "operatively linked" as used herein is intended to mean joined to the polymer by way of one or more covalent bonds or combined with the polymer and physically associated therewith without the formation of covalent bonds, such as through ionic attraction or through hydrogen bonding.

The polymers which can be included herein are biocompatible polymers having little or no pharmacologic activity on their own. The polymers, monomers and linking compounds are described in detail in above-recited copending application Ser. No. 07/726,301, now U.S. Pat. No. 5,219,564, which has already been incorporated herein by reference.

Briefly, the monomers which are useful herein include any functional units which can be covalently bound to the antifibrotic agent, or polymerized to form the backbone of the compounds described herein which can be operatively linked to the antifibrotic agent. For example, preferred monomers include ethylene and propylene glycol monomers, certain vinylic or polyphenolic type monomers, povidone and povidone derivatives, monosaccharides, and other monomers which have low levels of toxicity and little or no pharmacological activity in and of themselves. The preferred monomers include propylene glycol and povidone monomers, since these can be reacted with the antifibrotic agent with or without the linking molecule and have desirable solubility characteristics.

Suitable polymers which can be included herein are polymers comprised in whole or in part of the monomers referred to above. These are described in great detail in the above-noted copending application. As such, these may poly(oxyalkylene) polyacids, block copolymers of such polyacids with poly(amino acids), polyesters and other types of polymers.

The preferred polymers for use herein are polyalkylene oxides, and in particular, polyethylene and polypropylene glycols which are copolymerized with amino acids or peptide sequences, which can provide pendant functional groups, at regular intervals, for antifibrotic agent attachment or crosslinking. The polymer may contain covalent carbon-carbon, ether, ester, amine, amide, anhydride or urethane linkages.

The preferred poly(alkylene oxides) suitable for use herein include the polymers of PEG, polypropylene glycol, poly(isopropylene glycol), polybutylene glycol, poly(isobutylene) glycol and copolymers thereof. Hence, the backbone of the polymer typically contains straight or branched chain alkyl groups of up to four carbon atoms, with up to about 100 repeating units, with the preferred polymer containing about 10 to 100 repeating units.

The molecular weight of the polymer is not critical, and would depend mainly upon the end use contemplated. In general, the useful number average molecular weight is between about 600 and 200,000 daltons, and preferably about 2000 to about 50,000 daltons. Preferably the polymers used herein are hydrolytically stable; in this case, lower molecular weight polymers can be used. The most preferred polymers and copolymers included herein are the polyethylene glycols (PEGs) and PEG copolymerized with amino acids or peptides having multiple functional groups.

The preferred linking compounds used herein area amino acids and peptides which typically contain saturated or unsaturated straight or branched alkyl groups of up to about six carbon atoms, or alkylphenyl groups, the alkyl portion of which may be covalently bonded to an amine or other functional moiety. The amino acids, as well as the peptides having a low number of amino acids therein, e.g., up to about five, are preferably alpha amino acids, which are naturally occurring. The most preferred amino acids are those containing multiple functional groups, e.g., two amino groups. The most preferred amino acids are lysine, arginine and cHyp. Preferred peptides are those which can react with PEG or another polymer and bond via amide, ester or urethane linkages.

To conduct the polymerization reactions referred to above, one can employ various aspects of polymer chemistry to obtain polymers with little variation in the structure or physical parameters. One example of a polymerization technique which can be used to synthesize the polymers noted above is an interfacial polymerization between a water-immiscible organic solution containing one or more activated poly(allylene) oxides, and a water miscible phase containing one or more amino acids or peptides, having the appropriately protected C-terminals. The aqueous solution is buffered as appropriate, e.g., to a pH of about 8.0, and the organic phase is added. After reaction, the mixture can be acidified and separated, with the organic phase containing the polymer. It is also possible to form the copolymers noted above by using numerous alternative methods and reagents which are well understood by the artisan.

By selecting the appropriate starting materials, one can form a polymer having free hydroxyl, carboxyl or amino groups which are reactive with the antifibrotic agents or with the linking compounds. For example, when the polymer has pendant carboxyl groups, the antifibrotic agent may be directly conjugated with the carboxyl group via a hydroxyl or amino group. A protection-deprotection reaction scheme can be utilized to block the reactive groups of the antifibrotic agent, when multiple functional reactive groups are present which may react with the same reagent. Such a scheme allows for the formation of more numerous and more stable bonds; after which the deprotection step is undertaken. In the same manner, one or more functional groups which may be present on the polymer can also be protected.

When the polymer selected does not contain the linking molecule in the backbone, and it contains pendant carboxyl groups, or if it is otherwise desired, the polymer can be reacted with the linking compound prior to reaction with the antifibrotic agent. For example, pendant carboxyl groups can be reacted with a linking compound, e.g., an alkanolamine, under conditions which favor the formation of ester or amide bonds between these two compounds, after which the antifibrotic agent is added. The reaction between the polymer carboxyl groups and the linking compound can be conducted in the appropriate solvent and at the appropriate pH to favor the desired functional group formation. After this reaction, if not already in an organic solvent, the components can be transferred to an organic medium and a coupling reagent can be added, e.g., dicyclohexylcarbodiimide (DCC) with any appropriate acylating catalyst to conjugate the antifibrotic agent and the polymer.

The above order of reaction can also be reversed; the drug and the linking molecule are reacted, and then this reaction product is combined with the polymer under appropriate reaction conditions. This has been the approach taken in preparing a preferred polymer composition of the present invention. A dipeptide of L-Lys and cHyp is prepared separately from the preparation of bis(succinimidyl) poly(ethylene glycol), after which the two reactants are brought together to make the final polymer product, poly(PEG-Lys-cHyp amide). Synthesis of the dipeptide requires initial protection of the terminal α-amino and ε-amino groups of L-Lysine in order to restrict the coupling reaction to the nitrogen atom of cHyp, and deprotection after coupling with cHyp to form the L-Lys-cHyp dipeptide by means of an amide bond formed between the nitrogen atom of cHyp and the carboxyl group of L-Lys. The dipeptide is then brought together with bis(succinimidyl) poly(ethylene glycol) (BSC-PEG) in a buffered aqueous solution polymerization to produce a relatively high molecular weight, water-soluble polyurethane.

Another process for conjugating the polymer and the antifibrotic agent involves the reaction of pendant reactive groups with a compound having aldehyde, ketone or carboxyl groups. The polymer can be combined with a compound which forms acyl hydrazino groups, e.g, hydrazine, and the resulting acyl hydrazino moiety can be linked to the aldehyde, ketone or carboxyl groups, thus forming a hydrazone or diacyl hydrazide linkage between the copolymer and the active compound. Hydrazones can be formed with aldehyde or ketone containing drugs, or by oxidation of carbohydrate residues of glycopeptides.

The polymers noted above can optionally be crosslinked to modify the utility thereof, such as to render the compounds more or less water soluble. Numerous crosslinking agents can be mentioned as useful herein, including diols and higher polyols, polyamines, polycarboxylic acids, polyisocyanates and the like.

If the polymer is crosslinked, it may be desirable to complex the antifibrotic agent with the polymer rather than covalently bond the active compound to the polymer, either directly or via the linking compound, if adequate delivery of the antifibrotic compound can be realized at the site of activity. Thus, non-covalently bound forms are within the scope of the invention.

It is also desirable to include the monomers described above reacted with the antifibrotic agent, with or without one or more of the linking molecules included. In this aspect of the invention, the antifibrotic agent can be reacted directly with the monomer via any of the processes detailed above. The monomer is substituted for the polymer and reacted with antifibrotic agent and/or the linking compound. The monomer conjugated with the drug can then be used in the methods described below.

The method of treatment aspects of the invention involve the administration of a polymer or a monomer as noted above to a patient in need of such treatment, in an amount effective to modulate the metabolism of collagen, and thus reduce the formation of fibrotic tissue. As mentioned previously, this may entail any of numerous mechanisms of action, such as inhibiting the formation of collagen, enhancing the removal of collagen which is deposited in tissue abnormally and inhibiting the deposition of collagen in fibrotic tissue.

The compounds may be administered in doses ranging from about 0.05 mg/kg/day to as high as about 1–2 g/kg/day, by any appropriate route of administration, depending upon the particular condition under treatment. The exact dosages will be apparent to those skilled in the medical arts talking into account the teachings contained herein and the overall condition of the patient. Preferably once-daily dosage will be effective in treating patients for the disorders described herein, but divided daily dosages are acceptable as well.

One preferred method of treatment involves the administration of one or more of the antifibrotic agents described above to a mammalian patient with a pulmonary disease or disorder, such as pulmonary hypertension or pulmonary fibrosis. Pulmonary hypertension may accompany pulmonary fibrosis in some patients, or may be found independent of other pulmonary disease, such as in congestive heart failure or other hypoxic conditions. In this method of treatment, the antifibrotic agent may be administered in polymeric or monomeric form via any of the preferred routes of administration, e.g., oral, parenteral or aerosol, e.g., IPPB.

Another preferred method of treatment involves the administration of one or more of the antifibrotic agents described above to a mammalian patient with hepatic disease characterized by a defect in collagen metabolism, e.g, cirrhosis. In this method of treatment, the antifibrotic agent is preferably administered in polymeric or monomeric form via any of the oral or parenteral routes of administration.

Another preferred method of treatment involves the administration of one or more of the antifibrotic agents described above to a mammalian patient with a skin disorder, wherein collagen metabolism, e.g., excessive deposition is implicated. Examples of such skin disorders include the excess or abnormal formation of scar tissue, wrinkling, scleroderma and other conditions involving the skin. In this method of treatment, the antifibrotic agent is most preferably administered orally, parenterally, topically or transdermally.

Another preferred method involves the treatment of non-specific vascular diseases, wherein the compound including one or more of the antifibrotic agents described above is administered to a mammalian patient with atherosclerotic disease in an amount effective to treat abnormal collagen deposition or metabolism. Atherosclerotic disease involves the formation of atherosclerotic plaque and changes in the vascular tissue, such as thickening of the vessel walls, which may involve collagen to a greater or lesser degree. In this method of treatment, the antifibrotic agent is most preferably administered orally, parenterally, topically or transdermally. The invention described herein includes various pharmaceutical dosage forms containing the antifibrotic agents in polymeric or monomeric form. The pharmaceutical dosage forms include those recognized conventionally, e.g., tablets, capsules, oral liquids and solutions, drops, parenteral solutions and suspensions, emulsions, oral powders, inhalable solutions or powders, aerosols, topical solutions, suspensions, emulsions, creams, lotions, ointments, and transdermal liquids and the like.

Typically the dosage forms comprise from about 5 to about 70 percent active ingredient per dosage form. These may be packaged in multiple dose containers or unit dose packages.

Suitable solid carriers include those which are known e.g., magnesium carbonate, magnesium stearate, talc, lactose and the like. These carriers are typically used in oral tablets and capsules.

Oral liquids likely comprise about 5 to about 70 percent active ingredient in solution, suspension or emulsion form. Suitable carriers again are known, and include, e.g., water, alcohol, propylene glycol and others.

Aerosol preparations are typically suitable for nasal or oral inhalation, and may be in powder or solution form, in combination with a compressed gas, typically compressed air. Additionally, aerosols may be useful topically.

Topical preparations useful herein include creams, ointments, solutions, suspensions and the like. These may be formulated to enable one to apply the appropriate dosage topically to the affected area once daily, up to 3–4 times daily, as appropriate. Topical sprays may be included herein as well.

Depending upon the particular compound selected, transdermal delivery may be an option, providing a steady state delivery of the medication which is preferred in some circumstances. Transdermal delivery typically involves the use of a compound in solution, with an alcoholic vehicle, optionally a penetration enhancer, such as a surfactant and other optional ingredients. Matrix and reservoir type transdermal delivery systems are examples of suitable transdermal systems. Transdermal delivery differs from conventional topical treatment in that the dosage form delivers a systemic dose of medication to the patient.

A delivery system which may have particular utility in the present invention is one which utilizes liposomes to encapsulate or include the antifibrotic agent. In this system, the liposome may be targeted to a particular site for release of the antifibrotic agent or degradation of the polymeric or monomeric structure to release the active compound. This delivery system thus may obviate excessive dosages which are often necessary to provide a therapeutically useful dose of the drug at the site of activity. In selected experiments, and as set forth in the examples, the effective amount of the antifibrotic agent may be reduced by as much as twenty times the normal effective dose, as indicated by experimental protocols wherein the same antifibrotic agents are administered in free form.

Liposomes may be used herein in any of the appropriate routes of administration described above. For example, liposomes may be formulated which can be administered orally, parenterally, transdermally or via inhalation. Drug toxicity could thus be reduced by selective drug delivery to the affected site, e.g., a blood vessel wall, using liposomes, e.g., injected intravenously. If the drug is liposome encapsulated, and is injected intravenously, the liposomes employed will be taken up by vascular cells, and locally high concentrations of the drug could be released over time within the blood vessel wall, resulting in improved drug action.

The use of liposome encapsulated polymeric and monomeric antifibrotic agents finds utility in the treatment of pulmonary hypertension, its associated events and sequelae, such as, for example, polycythemia. Liposome encapsulation permits greater quantities of the effective agent to be administered without concomitant toxicity and thereby offers a viable therapeutic alternative.

The liposome encapsulated materials are preferably administered parenterally and, particularly may be administered by intravenous injection. A particularly preferred proline analog is cis-4-hydroxy-L-proline. The proline analogs of the present invention are generally disclosed in U.S. Pat. No. 4,428,939, issued. Jan. 31, 1984 to Darwin J. Prockop, the disclosure of which is incorporated herein by reference in its entirety. Such compounds are illustrative of antifibrotic agents useful in accordance with the present invention.

It has been demonstrated that twice daily subcutaneous injections of 200 mg/kg cHyp ameliorates development of chronic hypoxia-induced hypertension in rats. Since prolonged treatment with cHyp causes toxicity in adult rodents, localized delivery of cHyp to hypertensive pulmonary arteries has been achieved by encapsulation in phospholipid based liposomes. Rats with experimentally induced pulmonary hypertension have been successfully treated with liposome-encapsulated cHyp, reducing the effective dose of drug substantially, and causing sustained inhibition of vascular collagen accumulation.

The invention will be further demonstrated by the Examples set out further below; and for purposes of illustration, the following structural formulas are presented:

when cHyp is coupled to Nα,Nε-di-t-butoxycarbonyl-L-lysine-N-hydroxysuccinimide ester followed by deprotection, the following dipeptide Lys-cHyp is formed:

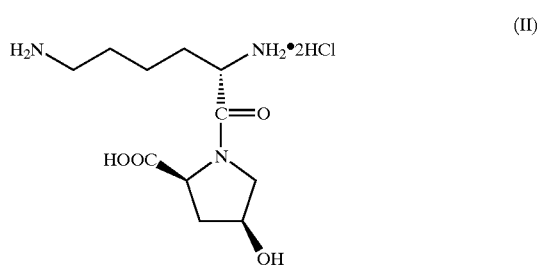

when a PEG copolymer is reacted with lysine, the following poly(PEG-Lys) copolymer is formed:

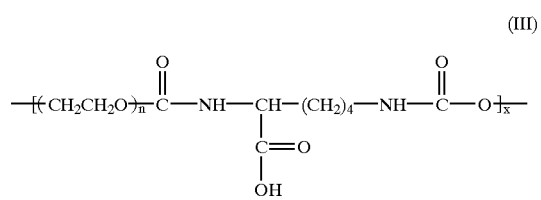

when BSA-PEG, bis(succinimidyl) poly(ethylene glycol), is reacted with the dipeptide Lys-cHyp, poly(PEG-Lys-cHyp amide) of the following formula is formed:

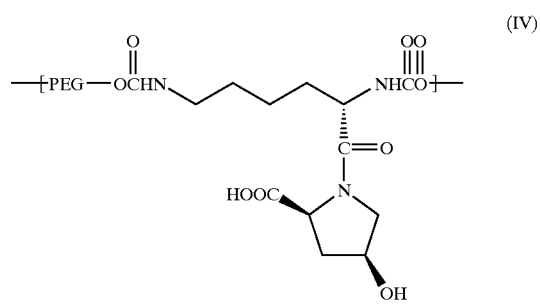

Likewise for purposes of illustration, the following reaction schemes show the preferred processes of malting the polymers of the present invention.

Scheme 1 illustrates the preferred method of preparing the cHyp based polymers of the present invention, in which the dipeptide, Lys-cHyp, reactant is formed separately from the BSA-PEG reactant, which is prepared in accordance with known methods, and solution polymerization of these two reactants gives the final product;

Scheme 2 involves the preparation of poly(cis-N-palmitate-Hyp) ester and is the subject of Example 13 below; the trans-N-palmitoyl hydroxyproline is reacted with triphenylphosphine and a dehydrating agent to form a bicyclic compound, which in turn opens and rearranges to the cis form, which can be polymerized;

Scheme 3 involves the preparation of monomethoxy-PEG-cHyp conjugates, and is described in detail in Example 14 further below;

Scheme 4 illustrates the preparation of poly(PEG-Lys)-cHyp copolymers, and is described in detail in Example 15 further below.

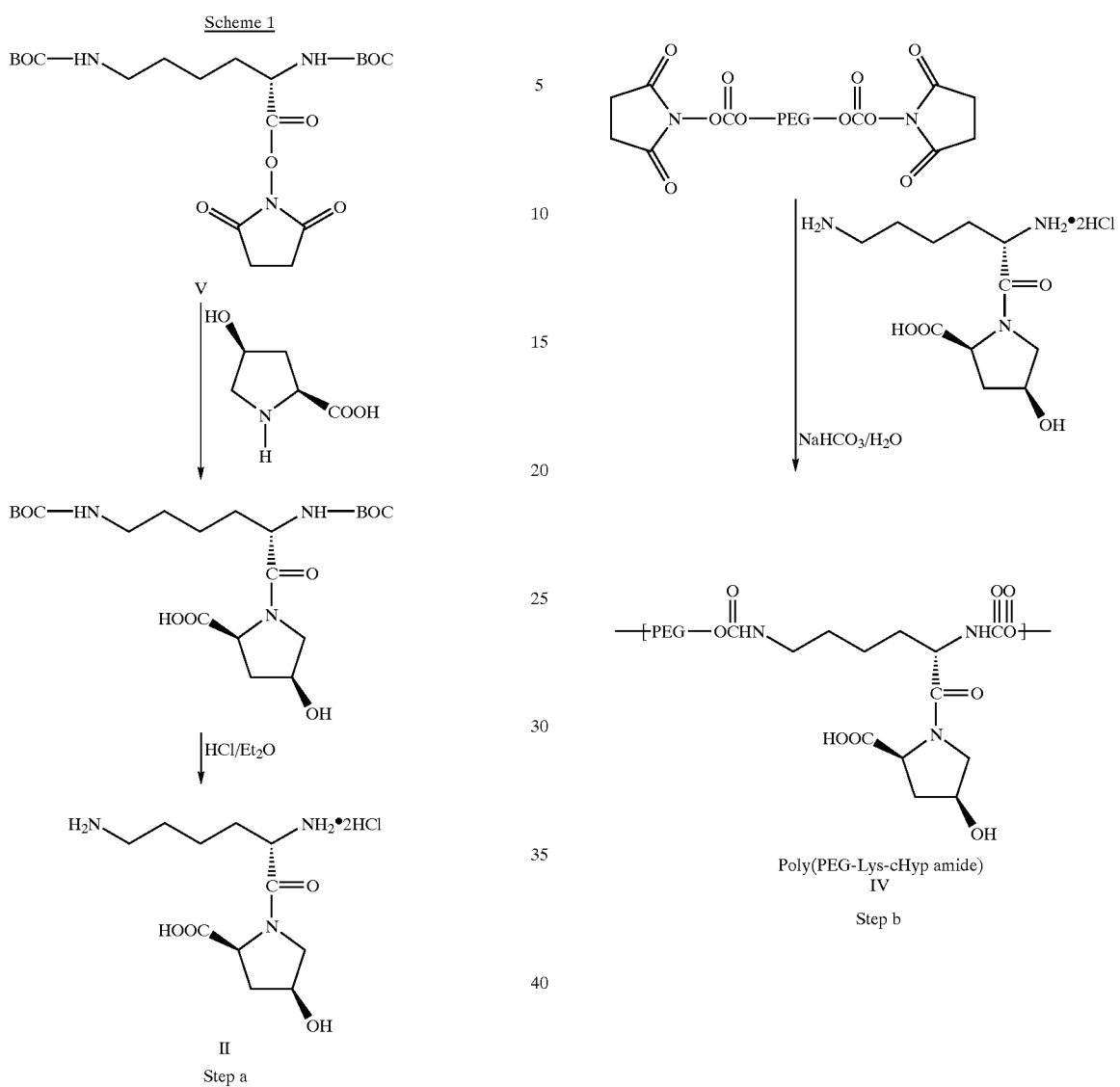
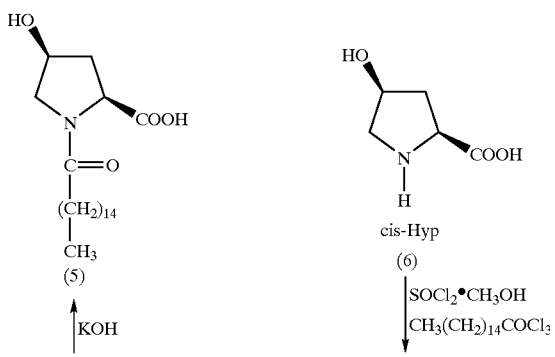

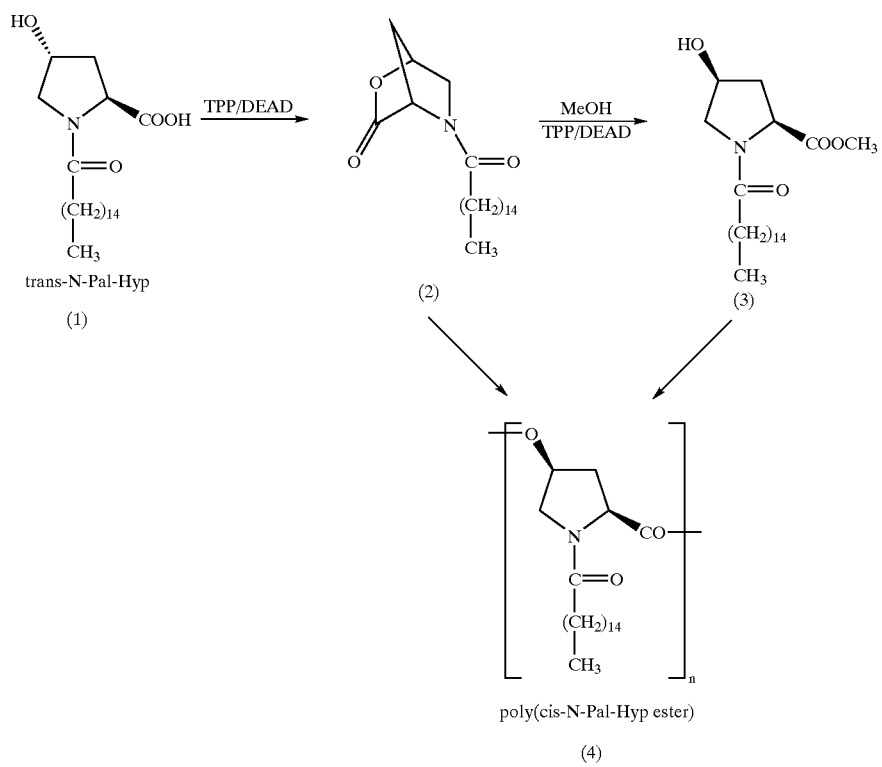
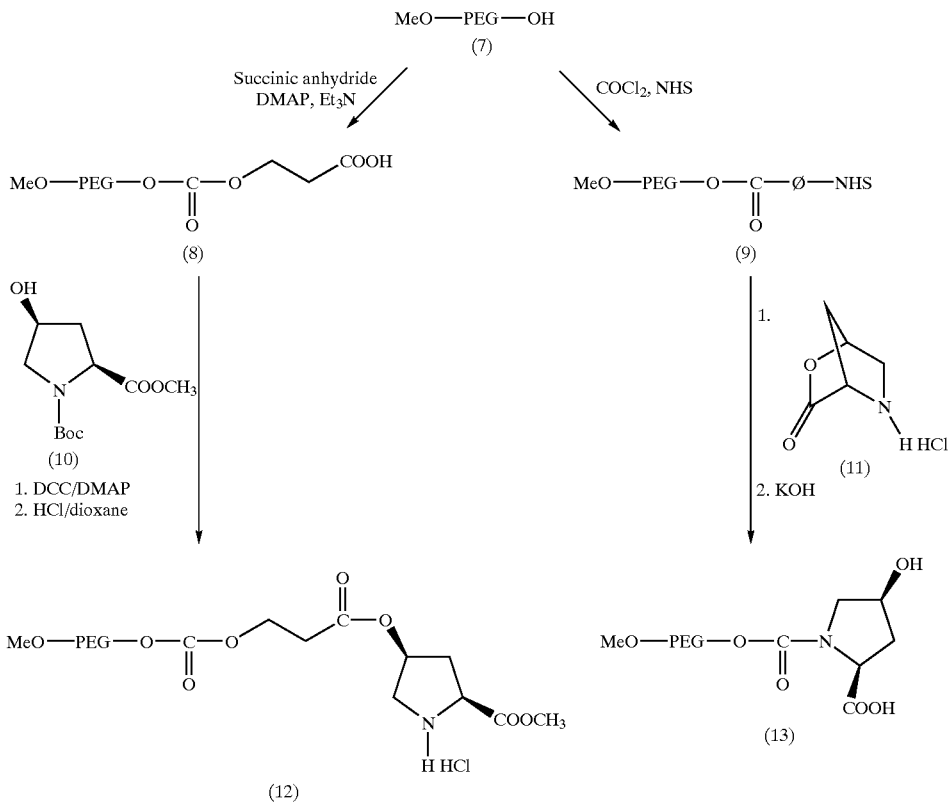
Scheme 3
Preparation of monomethoxy-PEG-cis-Hyp conjugates
Scheme 3a
Scheme 3b

19

Scheme 4
Preparation of poly(PEG-Lys)-cis-Hyp copolymers

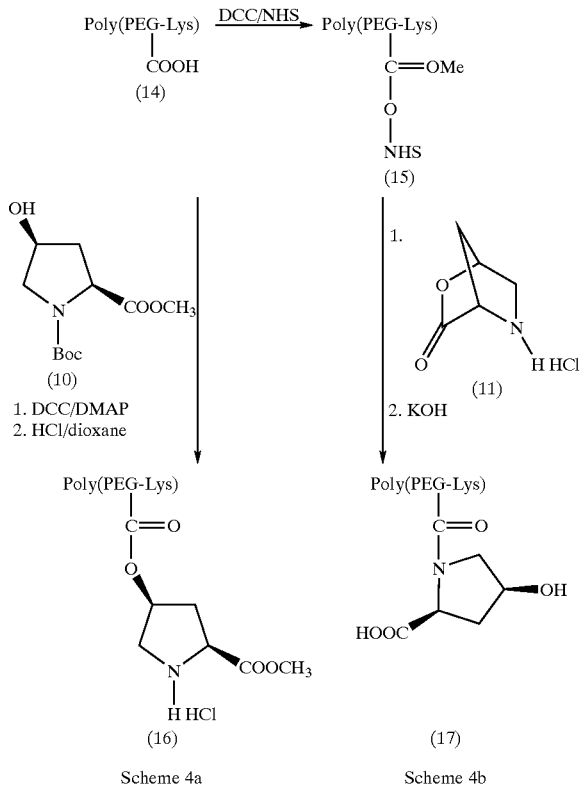

Scheme 4a      Scheme 4b

EXAMPLE 1

Preparation of PEG-Bis Succinimidyl Carbonate

The preparation. of PEG-bis succinimidyl carbonate is disclosed in Zalipsky et al., *J. Chem. Soc.*, 1991, 469:91. In a 250 mL round bottomed flask, 10 g (10 mmols of hydroxyl groups) of PEG 2000 (Fluka) was dissolved in 120 mL of toluene and the polymer solution was azeotropically dried for two hours under reflux, using a Dean-Stark trap. The polymer solution was then cooled to 25° C. and 15 mL (29 mmol) of a 20 percent solution of phosgene in toluene (1.93 M) was added. The reaction mixture was stirred at 25° C. overnight and then evaporated to dryness on a rotary evaporator (water bath temperature maintained at 40° C.). Another 100 mL of toluene was added and evaporated to remove all traces of phosgene. To the polymeric chloroformate was added 30 mL of dry toluene, 10 mL of methylene chloride, and 1.7 g (14.8 mmol) of N-hydroxy succcinimide, and the mixture was stirred vigorously. The reaction flask was then cooled in an ice water bath and 1.5 g (14.9 mmol) of triethylamine was added gradually. Immediate precipitation of triethylamine hydrochloride was seen. The cooling bath was removed and the stirring continued at 25° C. for five hours. Then 10 mL of toluene was added and the reaction mixture cooled to 4° C. to maximize the triethylamine hydrochloride precipitation.

The precipitate was filtered and the filtrate concentrated to about half of its original volume. The concentrated solution was then added to 60 mL of ether with stirring to precipitate the polymeric product. After cooling to 40° C., the crude product was recovered by filtration, dried, redissolved in 100 mL of 2-propanol at 45° C. and allowed to recrystallize. The product was recovered by filtration, washed with ether and dried under high vacuum. The recovery of the white crystalline solid was 74%.

EXAMPLE 2

Preparation of PEG-Lys Ethyl Ester Copolymer: Poly(PEG-Lys-OEt)

In a 500 mL three-necked round-bottomed flask fitted with an overhead stirrer was dissolved 1.1 g (4.4 mmol) of lysine ethyl ester hydrochloride salt (Fluka) and 1.7 g (21 mmol) of sodium bicarbonate in 100 mL of water. The PEG-N-hydroxy succinimide-dicarbonate of Example I (10 g, 4.4 meq) was dissolved in 200 mL of methylene chloride and added to the reaction mixture. The mixture was stirred vigorously (about 1100 rpm) for two hours and then acidified to about pH 2. The two phases were separated and the organic phase was washed twice with NaCl. The organic layer was then dried over anhydrous MgSO4, filtered and concentrated. The polymer was precipitated using cold ether, cooled to 40° C. and filtered to recover 6.7 g (67%) of the polymer.

The crude polymer (500 mg) was dissolved in 10 mL of distilled water and dialyzed against distilled water at room temperature for 48 hours using a SPECTRAPOR(™) membrane with a molecular weight cut-off of 12,000 to 14,000 daltons. The purified polymer was extracted with methylene chloride, washed with saturated NaCl solution, dried and evaporated to obtain 263 mg (53%) of pure polymer.

EXAMPLE 3

Preparation of PEG-Lys Copolymer: Poly(PEG-Lys)

The polymer of Example 2 (5 g) was dissolved in 5 mL of H$_2$O. The pH of the polymer solution was about 5 as measured with a pH meter. A 0.01N NaOH solution was prepared, and the base was added dropwise into the polymer solution with stirring. The pH was monitored continuously and kept around 11.5 by the addition of base as needed. The reaction was allowed to proceed for five hours, after which the reaction was stopped and the reaction mixture was acidified with 0.1 N HCl. The polymer was extracted into methylene chloride and the extract was washed with saturated NaCl, dried over anhydrous MgSO4, filtered and concentrated. The polymer was then precipitated with cold ether. After cooling for several hours, the product was collected in a Buchner funnel, washed with cold ether and dried under vacuum overnight, after which 3.5 g of polymer final product (71%) was recovered.

EXAMPLE 4

Preparation of Activated Poly(PEG-Lys)

In a 10 mL round-bottomed flask, 1.0 g (0.46 mmol) of the polymer of Example 3 was dissolved in 5 mL of methylene chloride. To this solution, 0.26 g of N-hydroxysuccinimide (Aldrich) (2.3 mmol) was added. The flask was cooled in an ice water bath and 0.10 g (0.50 mmol) of dicyclohexylcarbodiimide (DCC) (Aldrich) was added. The reaction mixture was then stirred at 0° C. for one hour and then at room temperature overnight. The reaction mixture was filtered to remove dicyclohexyl urea and the methylene chlorine was evaporated to give a white, waxy material. Isopropanol (5 mL) was added and the mixture was stirred until a clear solution was obtained. Cooling to −15° C. precipitated a white solid which was collected on a Buchner funnel and washed first with isopropanol and then with hexane. The material was further purified by recrystallization from isopropanol. The recovery of the final product was 0.72 g (71%).

EXAMPLE 5

Preparation of Poly(PEG-Lys) with Pendant Acyl Hydrazine

In a 50 mL round-bottomed flask, 2.2 g (1.0 mmol) of the polymer of Example 3 was dissolved in 20 mL of methylene chloride. The flask was then cooled in an ice water bath. To the flask were added 410 mg (2.0 mmol) of DCC and 260 mg (2.0 mmol) of tenn-butyl carbamate (Alrich). The contents of the flask were stirred at ice water bath temperature for 1 hour and then stirred at room temperature for 24 hours. The reaction mixture was filtered to remove the dicyclohexyl urea, followed by evaporation of the filtrate to dryness, which gave 1.5 g of light solid that was purified by recrystallization from 2-propanol. The $^1$H proton NMR spectrum of the white, waxy solid showed term-butyl peaks, and the total area involved correlated to >90% conversion. When redissolved in methanol and reprecipitated with ether, the relative intensity of this peak did not decrease.

An approximately 4 M solution of HCl in dioxane was prepared by bubbling HCl gas through dioxane in an Erlenmeyer flask (a 4.0 M solution is also available commercially from Pierce). In a 250 mL round-bottomed flask was placed 75 mL of the 4.0 M HCl/dioxane solution, and to this was added with stirring 5.0 g of the polymer-carbamate reaction product in the form of small pieces. Stirring was continued for two hours at room temperature. The polymer settled at the bottom of the flask as an oil. The dioxane/HCl layer was decanted and the polymer layer was added to 100 mL of the ether with stirring. The polymer precipitated and was isolated, washed twice with 50 mL of ether and dried under vacuum. It was further precipitated by recrystallization from isopropanol. The $^1$H NMR spectrum of the product showed the complete absence of term-butyl groups. Non-aqueous titration against sodium methoxide with methyl red as the indicator showed about 100% of the expected hydrochloride.

EXAMPLE 6

Preparation of Poly(PEG-Lys) Having Ethanol Amide Pendant Functional Groups

In a 50 mL round-bottomed flask, 0.400 g (0.1819 mmol) of the poly(PEG-Lys) of Example 3 was dissolved in 40 mL of water. To this solution was added 0.1 mL (1.656 mmol) of ethanol amine (Aldrich). The pH was adjusted to 4.75 by the addition of 0.1 N HC1. Then 0.348 g (1.82 mmol) of solid 1-(3-dimethylaminopropyl-3-ethylcarbodiimide) (Sigma) was added. The pH had a tendency to increase, but was maintained around 4.75 by the addition of 1 N HCl. After 30 minutes, no further increase in pH was observed. The reaction mixture was stirred overnight and then acidified and extracted into methylene chloride. The methylene chloride extract was washed with saturated sodium chloride solution, dried with anhydrous magnesium sulfate, filtered, concentrated to a viscous syrup and precipitated with cold ether. About 0.318 g of crude poly(PEG-Lys) with ethanol amide pendant functional groups was recovered. The crude product was purified by reprecipitation from isopropanol, followed by washings with hexane and complete drying in vacuo. Thin layer chromatography (TLC) in a 4:1 ratio solution of ethanol to ammonia showed an absence of free ethanolamine.

EXAMPLE 7

Preparation of Poly(PEG-Lys) Having Ethylamine Pendant Functional Groups

In a 100 mL three-necked flask, 1.21 g (0.55 mmol) of the poly(PEG-Lys) of Example 3 was dissolved in 80 mL of water. To this solution was added 0.37 mL (5.5 mmol) of ethylene diamine (Aldrich). The pH was adjusted to 4.75 by the addition of 1 N HCl. Then 1.05 g (5.5 mmol) of solid 1-(3-dimethylaminopropyl-3-ethylcarbodiimide) was added. The pH had a tendency to increase, but was maintained around 4.75 by the addition of 1 N HCl. After 30 minutes, no further increase in pH was observed. The reaction mixture was stirred overnight and then made basic and extracted into methylene chloride. The methylene chloride extract was washed with saturated sodium chloride, dried with anhydrous magnesium sulfate, filtered, concentrated to a viscous syrup and precipitated with cold ether. About 0.725 g of crude poly(PEG-Lys) having ethylamine pendant functional groups was recovered, which was purified by reprecipitation with isopropanol. TLC in a 2:1 solution of ethanol to ammonia showed an absence of free diamine.

EXAMPLE 8

Preparation of Poly(PEG-Lys) Having Pendant Hexylamine Functional Groups

The procedure of Example 7 was followed, but substituting 5.5 mmol of hexamethylene diamine (Aldrich) for the 5.5 mmol of the ethylene diamine. Upon purification of the product, TLC in a 2:1 ratio ethanol to ammonia solution showed an absence of free diamine.

EXAMPLE 9

Preparation of N-Benzylcarbamate Derivative of a Copolymer of PEG and Glutamic Acid Following the procedure of Example 1, 2 g of PEG 2000 were azeotropically dried by dissolving the polymer in 30 mL of toluene in a pre-weighed 50 mL round-bottomed flask provided with a stirrer. The polymer solution was azeotropically dried for two hours under reflux in an oil bath, the temperature of which was maintained at 140° C. All the solvent was distilled off and the product was dried in vacuo. The dried PEG was reweighed, dissolved in 5 mL of methylene chloride and stirred under argon. There was then added an equimolar amount of glutamic acid, the N-terminus of which was protected by a benzylcarbamate functional group (Sigma). Four times this amount of diisopropylcarbodiimide (Aldrich) and four times this amount of dimethylaminopyridinium toluene sulfonate (Aldrich) were added. The reaction mixture was heated slightly to dissolve the glutamic acid. The reaction was allowed to run for 24 hours at room temperature with stirring. A urea precipitate formed that was removed by filtration, and the product was precipitated by cold ether, filtered and dried under vacuum. About 1.6 g of polymer was recovered, which was purified by reprecipitation from isopropanol. TLC in a 5:5:1 ratio solution of toluene to acetic acid to water showed the absence of free glutamic acid.

EXAMPLE 10

Preparation of Poly(PEG-Lys)Cross-Linked by Hexamethylene Diisocyanate

A mold was prepared by clamping two square glass plates together, one of which had a 5 cm diameter circular cavity. The contacting surfaces of the glass plates were coated with trimethylchlorosilane (Aldrich) to prevent adhesion. The mold was placed on a level surface inside a glove box and further leveled using a carpenter's level. In a 100 mL beaker, 1.5 g of the poly(PEG-Lys) having pendant acyl hydrazine groups (0.67 mmol of hydrazine groups) of Example 5 was dissolved in 40 mL of methylene chloride. To this solution was added 1.5 g of finely powdered sodium bicarbonate. The suspension was stirred for one hour and the supernatant was tested for the presence of chloride ions with silver nitrate. A few drops of the methylene chloride solution were placed into a test tube, the methylene chloride was evaporated, and the residue was reacted with a few drops of silver nitrate solution acidified with nitric acid. The absence of any white turbidity indicated the complete neutralization and removal of hydrochloric acid.

The solution was then filtered and the residue was washed with methylene chloride. To the combined filtrate, 54 μL of hexamethylene diisocyanate (56 mg., 0.67 meq of isocyanate groups) (Aldrich) was added with stirring. After two to three minutes of stirring, the solution was poured into the circular cavity of the solvent casting mold. The cavity of the mold was covered with filter paper so that the solvent evaporation was slow and uniform. The film was allowed to dry in the glove box for 48 hours and then peeled from the mold. The thickness of the membrane was measured with an electronic vernier caliper inside the glove box and was found to be about 0.1 mm. The membranes obtained were semi-transparent and were somewhat hygroscopic, curling up when exposed to moisture in ambient air. When placed in water, the size of the films doubled in all dimensions, indicating a very large swelling ratio. The swollen membranes were transparent.

The membrane was assayed with trinitrophenyl sulfonic acid (TNBS) (Fluka) to determine the extent of crosslinking. An excess of TNBS was used, and after reacting with the polymer, the unreacted TNBS was allowed to react with an excess of adipic hydrazide. The IR absorbance obtained at 500 nm was then used to calculate the amount of free hydrazides present on the cross-linked membrane. Using this method, it was found that 80–85% of all available hydrazides participated in cross-linking, leaving only 15–20 percent of unreacted hydrazides on the cross-linked membrane. Calorimetry of the cross-linked membrane showed a sharp endothermic transition at 33.4° C. This is very similar to the $T_m$ of the corresponding non-cross-linked poly(PEG-Lys) having pendant acyl hydrazine functional groups (34.1° C). When the membrane was heated in an oven above the phase transition temperature, it became very flexible but did not disintegrate. These results indicate that the properties of PEG dominate even after copolymerization with lysine and cross-linking.

Swelling measurements of the membrane were made by two methods. The dimensions of the dry membrane were measured and the membrane was allowed to swell in water. The increase in dimension was taken as a measure of swelling. Alternately, the membrane was weighed before and after swelling and the increase in weight was taken as a measure of swelling. Both methods indicated that the membrane absorbs about 5 to 8 times its weight of water. The tensile strength of the membrane was measured using strips of membrane 0.07 mm thick, 5 mm wide and 50 mm long. Measurements were made employing both dry and swollen membranes. In the swollen state, the membrane behaves like a perfect elastomer. The membrane did not exhibit a yield point and a plot of stress against strain gave a straight line.

The stability of the membrane was investigated in acidic, basic and neutral media, the results of which are illustrated in Table 1 below. Small specimens of the membrane were placed in contact with a number of aqueous solutions of varying pH at room temperature and the time required for the complete disappearance of the membrane was noted. The membrane was generally found to be more stable in weakly acidic media and extremely unstable in alkaline media.

TABLE 1

| SOLUTION | TIME REQUIRED FOR DISAPPEARANCE |
| --- | --- |
| 1N HCL | 5 to 8 days |
| 0.1N HCL | No change in 8 days |
| 0.01N HCL | No change in 8 days |
| Deionized water | No change in 8 days |
| Borate (pH = 9) | 5 to 8 days |
| 0.01N NaOH | Less than 5 hours |
| 0.1N NaOH | Less than 5 hours |
| 1N NaOH | Less than 1 hour |

To test the stability under physiological conditions, an accelerated stability study was performed in which samples of membrane were exposed to phosphate buffer of pH 7.4 at 60° C. Under these conditions, the membrane lost weight at the rate of about 1 percent per hour. After 60 hours, the membrane disintegrated and became soluble in the buffer.

EXAMPLE 11

Preparation of Poly(PEG-Lys) Membranes Cross-Linked with Tris(Aminoethyl) Amine In a 100 mL beaker, 1.87 g of the PEG bis(succinimidyl carbonate) of Example 1 was dissolved in 20 mL of methylene chloride. In another beaker, 82 μL (89 mg) of tris (aminoethylamine) was dissolved in 20 mL of methylene chloride. The triamine solution was added to the PEG solution with vigorous stirring. After about five minutes, films were cast of the solution following the procedure described above with respect to Example 16. Swelling measurements of the membrane were then made by the two methods described above with respect to Example 16. Both methods indicated that the membrane absorbed about six times its weight of water.

The stability of the membrane was investigated in acidic, basic and neutral media as described above. In sodium hydroxide (0.01 and 0.1 N) the membrane disintegrated within a few hours. In acidic media and in phosphate buffer (pH 7.4) the membrane appeared to be stable for longer periods of time. The accelerated degradation study of Example 10 was also performed, in which the membrane remained intact for more than a week. An analysis of the buffer in which the accelerated stability study was conducted revealed that during the first 24 hours a small amount of PEG chains had leached from the crosslinked membrane, but throughout the following 72 hours, no more PEG was leached.

EXAMPLE 12

Preparation of Poly(Caprolactone) Semi-IPN's of Poly-(PEG-Lys) Membranes Cross-Linked by Diisocyanate The poly(PEG-Lys) membrane cross-linked by diisocyanatohexane was prepared as in Example 10, using 210 mg of the poly(PEG-Lys) of Example 5 having acyl hydrazine functional groups, dissolved in 10 mL of methylene chloride. The free base was formed with sodium bicarbonate, and the solution was then filtered. Prior to the addition of 4 µL (3.9 mg) of the hexamethylene diisocyanate, 0.47 g of poly(caprolactone) (Union Carbide) (mw 72,000) was added to the filtrate, which was stirred for 30 minutes to dissolve the polymer completely. The poly (PEG-Lys) was cross-linked and films were cast following the procedure described above with respect to Example 16. The resulting membrane was hydrophilic and absorbed water with an equilibrium water content of 36%, whereas films made of poly (caprolactone) alone were hydrophobic.

EXAMPLE 13

A. Poly(cis-N-Pal-Hyp Ester)

A poly(cis-N-Pal-Hyp) ester was prepared by melt transesterification of cis-4-hydroxy-N-palmitoyl-L-proline methyl ester (3) in the presence of aluminum isopropoxide (1% w/w), following a method described in Kohn et al., *J. Am. Chem. Soc.*, 1987, 109:817, for the polyesterification of N-protected trans-hydroxy-L-proline (see Scheme 2). The monomer (3) was prepared from cis-hydroxy-L-proline (6) by conventional methods, and could also have been prepared from trans-N-Pal-Hyp (1) by reaction with triphenylphosphine (TPP) and diethyl azodicarboxylate (DEAD), via the bicyclic lactone (2), as described in Papaioannu et al., *Acta Chem. Scand.*, 1990, 44:243.

B. Poly(Ethylene Glycol)-cis-Hyp Conjugates (12) and (13)

Cis-N-Boc-L-proline methyl ester (10) was esterified with the succinic ester of monomethoxy-PEG (8) in presence of DCC/dimethylaminopyridine (DMAP), followed by deprotection of the cis-Hyp-N-terminus with a 4N HC1/dioxane solution to yield the conjugate (12) (see Scheme 3a). Conjugate (13) was prepared by reaction of the succinimidyl carbonate activated monomethoxy PEG (9) with the lactone (11), followed by hydrolysis of the lactone in 2N KOH (see Scheme 3b). Lactone (11) was prepared from trans-N-Boc-Hyp as described for compound (2) (see Scheme 2), followed by deprotection of the N-terminus with 4N HCl/dioxane.

C. Poly(PEG-Lys-cis-Hyp) Copolymers (16) and (17)

The title compounds were prepared by covalent attachment of the Hyp derivatives (10) and (11) to the pendant side chains of poly(PEG-Lys) as described for the PEG conjugates (12) and (13) (see schemes 4a and 4b). The extent of cis-Hyp attachment to the poly(PEG-Lys) copolymer was assessed by the ratio of Lys to Hyp as determined by amino acid analysis.

D. Polyethylene Glycol-cHyp Conjugated- 1:2 Ratio

Polyethylene glycol may be conjugated with cHyp according to the reaction scheme depicted in Scheme 3a, resulting in a conjugate containing two cHyp moieties. As shown in the reaction pathway, the cHyp hydroxyl groups may be reacted with a conjugate of PEG and succinic acid, thus forming multiple ester linkages. The cHyp carboxylic acid group can be protected with a methoxy group or another suitable protecting group.

In the reaction scheme depicted in Scheme 3b, the PEG is linked to two cHyp moieties through urethane linkages.

Analysis and Evaluation: Poly(cis-4-Hydroxy-N-Palmitoyl-L-Proline Ester)

Since only the cis isomer of Hyp is pharmacologically active, the polymerization conditions were analyzed for effects on the retention of the cis configuration. The polymerization reaction was performed at temperatures ranging from 180° to 210° C. Polymers of highest molecular weight ($M_w$=21,600, $M_n$=15,900) were obtained when the reaction was conducted at 195° C. for 5 hours. All polymers were then hydrolyzed in 1M NaOH and the conformation of Hyp formed during hydrolysis was determined by $^{13}$C NMR.

A comparative hydrolysis of poly(trans-N-Pal-Hyp ester) obtained by the same method at 180° C. from trans-N-Hyp-Me showed that only trans-Hyp was formed. In contrast, hydrolysis of the polyester obtained from the cis monomer led to mixtures of cis and trans isomers, which could be resolved due to a chemical shift difference of almost 1 ppm between the pyrrole ring carbons of the two isomers. Comparing the peak heights of $^{13}$C NMR spectra to a calibration curve obtained from mixtures of known compositions, facilitated a quantitative analysis of the hydrolysis mixtures, which are illustrated in Table 2 below.

TABLE 2

Effect of Polymerization Conditions

| T (° C.) | Time (h) | Mw | Mn | cis/trans ratio |
|---|---|---|---|---|
| 180 | 17 | * | * | 9/1 |
| 195 | 5 | 21,590 | 15,856 | 3/1 |
| 210 | 17 | 14,224 | 10,166 | 1.8/1 |
| 210 | 5 | 15,644 | 11,377 | not det'd |

*Mw and Mn could not be determined due to the high polydisperisty of the sample.

Since increasing the reaction temperature favored the undesirable formation of trans-Hyp, reaction conditions were optimized at 180° C. Polymers of very low molecular weight were obtained. At 210° C., polymers with a low cis/trans ratio were formed. However at 195° C., it was possible to prepare relatively high polymers which consisted predominately of cHyp.

Alternatively, a ring opening polymerization reaction can be run using the bicycle lactone (2). The polymerization reaction was performed at 140° C. for variable periods of time (15 hours to 5 days), using aluminum isopropoxide as the catalyst. This procedure gave low molecular weight polymers that consisted of an almost equimolar mixture of cis- and trans-N-Pal-Hyp (cis/trans ratio: 0.9/1). Attempts to synthesize the target polymer using a coupling agents, such as DCC, in a direct coupling reaction failed due to the formation of the bicyclic lactone (2), via intramolecular esterification.

EXAMPLE 14

Attachment of Cis-Hyp to Poly(Ethylene Glycol) Derivatives

Due to their physicochemical and biological properties, poly(ethylene glycols) (PEGs) are promising drug carriers. Attachment of PEG to proteins was found to increase blood circulation time of the PEG-protein conjugates and to delay clearance by the RES.

Attachment of cis-Hyp has been by way of two different poly(ethylene glycol) based carriers. In the first case, cis-Hyp was attached to a monomethoxy-PEG ($M_w$=5,000) unit leading to new cis-Hyp conjugates having a 1:1 ratio of PEG to cis-Hyp (see Schemes 3a and 3b). In a similar fashion cis-Hyp was attached to poly(PEG-Lys), a new polymeric drug carrier. In poly(PEG-Lys), PEG chains and L-lysine are connected via urethane bonds in a strictly alternating fashion. The carboxylic groups of the lysyl residue provide convenient anchors for the attachment of the pendant ligands. Cis-Hyp was bound to the PEG based carrier by labile ester bonds (see Scheme 4a) and by more stable amide bonds (see Scheme 4b).

Any of the antifibrotic agents other than cHyp can abbe liposome encapsulated and administered to treat fibrotic conditions. Each of the antifibrotic agents can be administered in liposomes in an amount effective to treat diseases where collagen metabolism is of concern. The antifibrotic agents can also be linked to a monomer and incorporated into liposomes. For purposes of illustration, in the following composition the antifibrotic agent is cHyp linked to ethylene glycol:

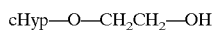

cHyp—O—CH$_2$CH$_2$—OH

The linkage could also be an ether, ester or some other linkage. Also, an additional antifibrotic compound can be linked to the glycol through the hydroxyl group. If ethylene glycol is used as the monomer, safety and toxicity may need to be taken into account. A preferred monomer in this regard would be propylene glycol or another suitably non-toxic monomer. A polymeric form which can also be included herein is the polymer:

cHyp-PEG or

cHyp-(PEG-cHyp)$_n$

The cHyp can be linked directly to the polymer or through a linking compound. Also, the cHyp can be substituted in whole or in part with another antifibrotic agent. The variable "n" in this case can be an integer of from 1 up to about 100.

Figure 6:
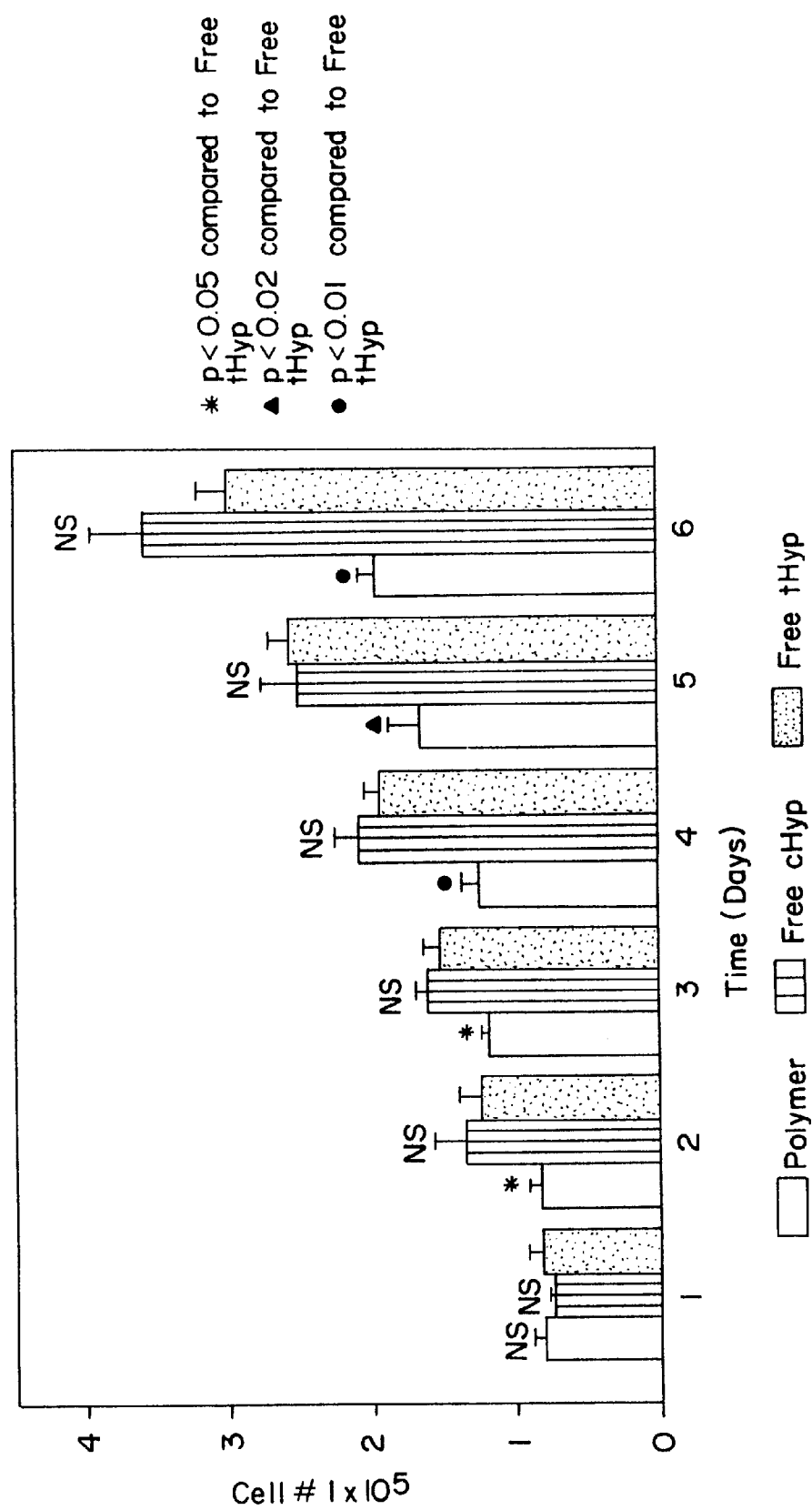
FIG. 6 is a graph of smooth muscle cell proliferation in the presence of polymeric polyethylene glycol (MW 2000)—lysine chemically reacted with cHYP via ester linkages.
Figure 7:
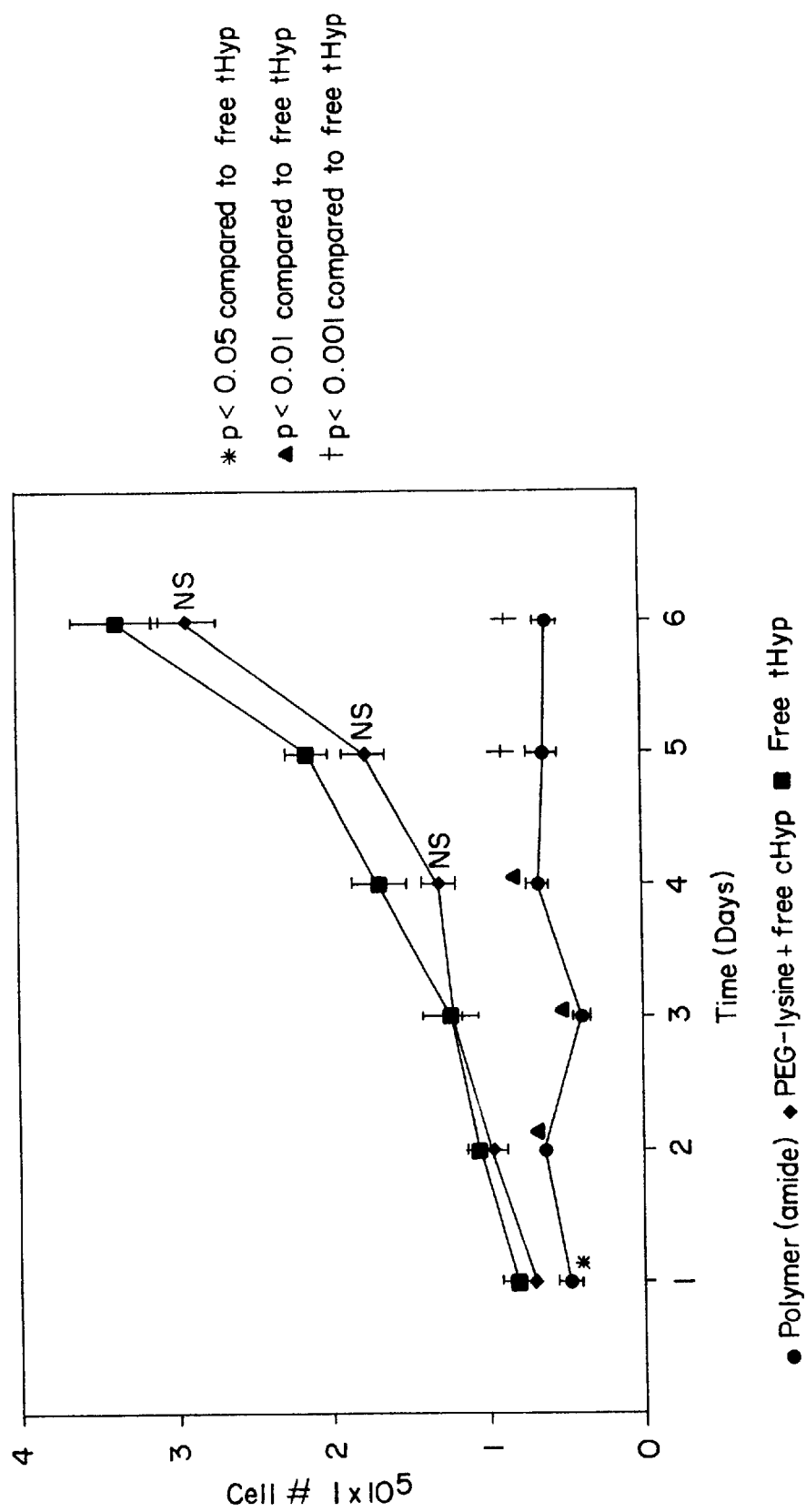
FIG. 7 is a graph of smooth muscle cell proliferation in the presence of polymeric polyethylene glycol (MW 2000)—lysine chemically reacted with cHYP via amide linkages.
Figure 8:
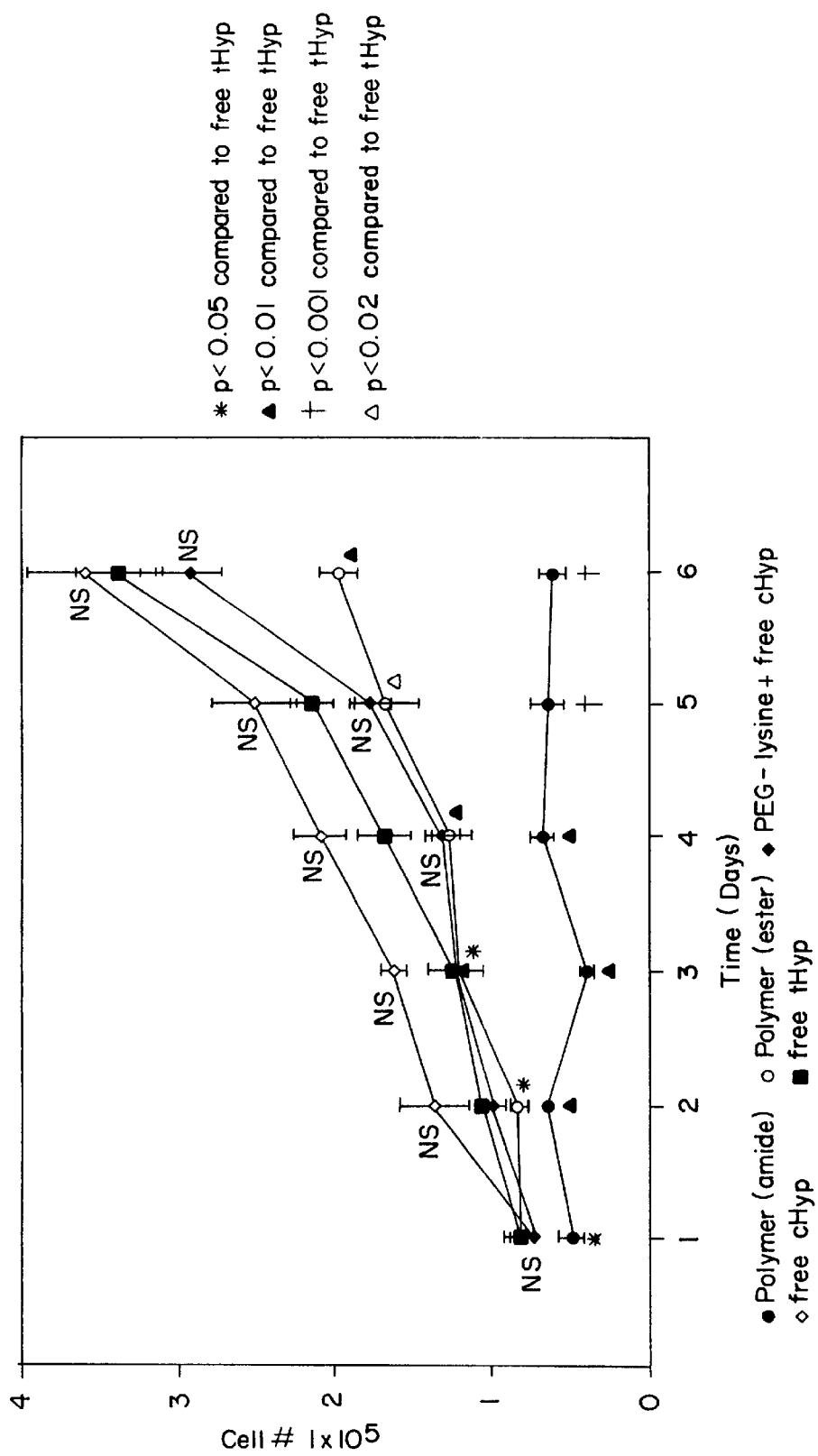
FIG. 8 is a comparison of the smooth muscle proliferation in the presence of ester linked cHYP and amide linked cHYP. Both polymeric forms are compared to PEG lysine and free cHYP, free cHYP and free tHYP, which is without substantial biological activity.
Figure 9:
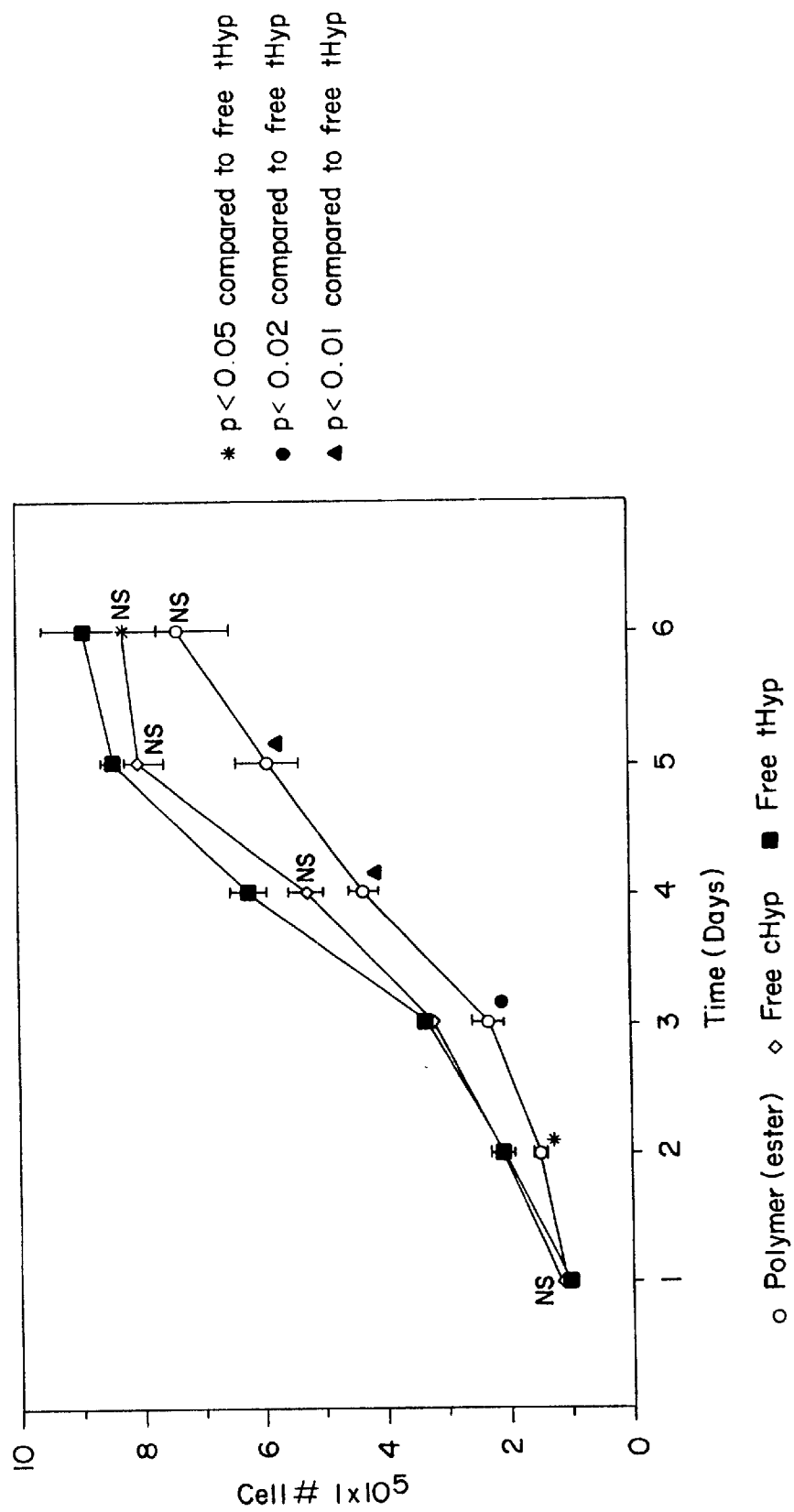
FIG. 9 is a graph of cell proliferation using rat lung fibroblasts in the presence of polyethylene glycol-lysine linked to cHYP via ester linkages.

As can be noted with respect to FIGS. 6–9, the antifibrotic agents can be conjugated with PEG or another polymer and used to reduce cellular proliferation in the presence of collagen metabolism. In FIG. 6, the effect of free cHyp, polymeric cHyp and free trans-hydroxyproline were compared over a six day period. Smooth muscle cells were allowed to proliferate in the presence of free cHyp, polymeric cHyp and trans-hydroxyproline. The polymeric cHyp was produced as described above and contained ester linkages. On each day, the cells were trypsinized and counted with a hemocytometer. Cellular proliferation was significantly reduced in the cHyp polymer group, as compared to the free cHyp and tHyp groups. This is further supported by the data illustrated in FIG. 9, generated with fibroblast cells. When the polymer is conjugated with cHyp via amide linkages, cellular proliferation is further reduced. See, e.g., FIG. 7, which presents a comparison of activity between the ester linked polymer and the amide linked polymer in FIG. 8.

EXAMPLE 15

Liposome Encapsulation

The encapsulation of drugs into liposomes may proceed in accordance with known techniques. An example of the preparation of the liposome encapsulated proline analogue of the invention follows: Small unilamellar liposomes were prepared by reverse phase evaporation using the method of Szolca and Papahadjopoulos as modified by Turrens and associates. A stock solution containing 97.5 mg L-alpha-dipalmitoyl lecithin, 24.2 mg cholesterol, and 9.6 mg stearylamine in a 14:7:4 molar ratio was dissolved in 5 ml of chloroform in a 50 ml round bottom flask. To this mixture, 50 mg of cHyp dissolved in 2.5 ml of 10 mM phosphate-buffered saline (PBS), pH 7.4, was added. The mixture was sonicated (model W-385 Ultrasonic Processor, Heat Systems-Ultrasonics, Inc., Farmingdale, N.Y.) at a power output of 7 for 1 min at 10° C. The mixture was converted to a homogeneous milky emulsion which was slightly viscous. The emulsion was transferred to a 50 ml rotary evaporation flask and volume was reduced under vacuum (400 torr) while maintaining the temperature at 25° C. When the emulsion became viscous and did not pool in the flask, 1.25 ml PBS was added. The evaporation was continued at 40° C. until the odor of chloroform was no longer detected and a free flowing turbid suspension was present. The suspension was kept at 4° C. overnight, centrifuged at 100,000×g for 35 min at 4° C., and recentrifuged after suspending the pellet in 6.5 ml of PBS. Prior to injection, the pellet was stored at 4° C. in 2.5 ml of PBS (40 $\mu$mol phospholipid/ml), filtered (0.22 $\mu$m Nalgene filter), and then passes serially through 18, 25 and 30 gauge needles.

The size profile of each batch of liposomes was determined by a fluorescent activated cell sorter (Coulter Epic 753 Dye Laser System, Coulter Electronics, Hyaleah, Fla.) from linear and logarithmic forward angle light scattered signals at 488 nm at 1000 mwatts. Latex beads (0.1, 0.22 and 0.51 $\mu$ in diameter) were used as size markers and approximately 20,000 signals were acquired per measurement. Since the charge, size and structure of L-proline is similar to that of cHyp, encapsulation efficiency of cHyp was estimated from the percent entrapment of 10 $\mu$Ci of [$^{14}$C]-L-proline into the liposome pellet following centrifugation.

EXAMPLE 16

Liposome Encapsulated cHyp Administration

In this example, the liposome encapsulated antifibrotic agent of the invention was tested and compared with alternative formulations and modes of administration of the same antifibrotic agent. Accordingly, the proline analogue cis-4-hydroxy-L-proline (cHyp) entrapped in liposomes was administered to rats developing hypoxic pulmonary hypertension.

METHODS

Materials

Materials were L-$\alpha$-dipalmitoylphosphatidylcholine (780 g/mol) (Avanti Polar Lipids, Birmingham, Ala.), cholesterol (386.6 g/mol) and stearylamine (269.5 g/mol) (Sigma Chemical Co., St. Louis, Mo.), cis-4-hydroxy-L-proline (cHyp) (Calbiochem Corp., La Jolla, Calif.), [$^{14}$C]-L-proline (260 mCi/mM) and methanol and quaternary ammonium hydroxide (Protosol, New England Nuclear Co., Boston, Mass.), fluorescent latex microspheres (Fluoresbrite, Polysciences, Inc., Warrington, Pa.), 1,1', dioctadecyl-3,3,3', 3'-tetra-methylindorbocyanine perchlorate (D282, Molecular Probes, Inc., Eugene, Oreg.), and rabbit anti-factor VIII antibody and FITC goat-anti-rabbit antibody (Calbiochem Corp., La Jolla, Calif.). Chemicals were analytical grade.

Animals

Six week old male Sprague Dawley rats (Crl:CD[SD]BR) weighing 185–205 g and 8 week old female Swiss mice (Crl:CP-1[ICR]BR) weighing 30–32 g (Charles River Breading Laboratories, Wilmington, Mass.) were maintained in a holding area one week prior to study and were fed food and water ad libitum. Rats were randomly allocated to hypoxia or air groups; mice breathed air. Animals were kept in a 12-hour light-dark cycle.

Exposure Conditions

Four rats were placed in a polycarbonate chamber measuring 51×41×22 cm, and humidified gas (10% $O_2$, 90% $N_2$ flowed into the chamber at a rate of 400 ml/min. Gas samples were analyzed electrometrically (model MB53-MK2, Radiometer, Copenhagen, Denmark); $PO_2$ ranged from 74–80 mmHg and $PCO_2$ from 3–5 mmHg. Air-breathing rats were kept in cages in the same room and were pair-fed to hypoxic animals by weighing the food consumed by hypoxic animals and feeding the same amount of food to air-breathing animals to ensure similar final body weights. The chambers were opened once daily for 10 min. to clean, weigh and feed the animals.

Hemodynamic Measurements and Heart Weight

A catheter was placed in the right ventricle of anesthetized rats (50 mg/kg pentobarbital intraperitoneally), and mean right ventricular pressure was measured using a pressure transducer (model P23Db, Statham, Instruments, Oxnard, Calif.) and recorded (model SP-2006, Statham Instruments). Pressure was measured after the animal had breathed air for 20 min. to eliminate the tonic response to hypoxia. After sacrifice by abdominal aorta transection, hematocrit and ratio of ventricular weights were measured, and the position of the catheter was confirmed at autopsy.

Biochemistry

Main pulmonary artery (9 mm in length) was excised and analyzed for total protein and hydroxyproline contents as previously described. Tissue was hydrolyzed in 6N HCl at 118° C. for 48 hrs., diluted 1:10 in water, and a 0.1 ml aliquot was assayed for total protein by the ninhydrin method using leucine as standard and for hydroxyproline by a calorimetric method. Results of triplicate measurements were expressed as content per vessel.

Preparation of Liposome

Unilamellar, positively charged phospholipid vesicles (liposomes) were prepared by reverse phase evaporation as previously described, except that the lecithin component was replaced with 97.5 mg L-α-dipalmitoylphosphatidylcholine.

Characterization of Liposomes

Liposome diameter was estimated by a single beam fluorescent activated cell sorter (Epic 752 Dye Laser System, Coulter Electronics, Hialeah, Fla.) using an argon ion laser emitting a 488 nm (1 watt). Latex microspheres (0.10–0.51 μm diameter) were used as size markers. Liposomes or microspheres were suspended in PBS, and size histograms were analyzed using a computer system (Easy 88 Epinet, Coulter Electronics) interfaced with the fluorescent activated cell sorter. The diameter of 90% of the liposomes ranged between 0.10 to 0.22 μm. Entrapment efficiency of cHyp into liposomes was estimated by substituting 10 μCi [$^{14}$C]-L-proline in place of cHyp (see above). A 0.1 ml aliquot of the [$^{14}$C]-L-proline entrapped liposome was added to 5 ml scintillation fluid (Liquiscint, National Diagnostics, Somerville, N.J.) and counted at 94% efficiency using a liquid scintillation counter (Tri-Carb, Packard Instruments, Downers Grove, Ill.). Percent encapsulation was estimated as the percentage of counts in liposomes and was found to be 51±6% (n=11) and remained constant during storage at 4° C. for 21 days.

Injections

Cis-4-hydroxy-L-proline dissolved in saline (free cHyp) or saline alone were injected subcutaneously (0.5 ml) or intravenously. Intravenous injections were performed in anesthetized animals (25 mg/lcg thiopental, intraperitoneally). In rats, liposomes containing cHyp or empty liposomes were injected intravenously (18 μmol phospholipid in –0.5 ml) via the dorsal vein of the penis over 5 sec using a 30 gauge needle. In mice, liposomes ( 18 μmol phospholipid in 0.5 ml) were injected into the tail vein.

Mode of Delivery and Dose of cHyp

Four modes of delivery of cHyp were used in rats. Free cHyp (200 or 100 mg/kg) was injected subcutaneously twice daily during exposure to hypoxia. A single dose of free cHyp (200 mg/kg) was given intravenously prior to exposure to hypoxia. Single doses of cHyp entrapped in liposomes (200 or 100 mg/kg) were injected intravenously prior to exposure to hypoxia. Multiple doses of cHyp in liposomes (200 mg/kg) were injected intravenously prior to hypoxia and every 5 days during exposure to hypoxia. Single doses of cHyp entrapped in liposomes after reticuloendothelial blocage were produced by intravenous injection of a single dose of empty liposomes followed 30 minutes later by a single intravenous dose of cHyp entrapped in liposomes (100 or 50 mg/kg) prior to exposure to hypoxia. The purpose was to enhance the localization of liposomes containing cHyp to the lungs by prior treatment with empty liposomes as temporary reticuloendothelial blocking agents.

General Protocol

In each animal, we assessed the effect of injection of cHyp on five parameters of exposure to hypoxia: mean right ventricular pressure (RVP) measured after the animal had been removed from the hypoxic environment, ratio of ventricular weights (RV/[LV+S]), hematocrit, and the contents of hydroxyproline and protein in the pulmonary artery. For each experimental group, comparisons were made to a group exposed to hypoxia and injected with a control substance and to a group exposed to air. For free cHyp, the control substance was saline; for cHyp entrapped in liposomes, the control substance was empty liposomes. Groups were age-matched; the air group was weight-matched to the hypoxic group injected with the control substance. Average results of each parameter were compared.

Experimental Protocols

Twelve groups of rats were exposed to hypoxia and injected with cHyp (Groups 1–12, Table 3, further below); three groups were exposed to air and injected with cHyp (Groups 13–15, Table 3, further below). Groups were used to compare the mode of delivery of cHyp, various doses using the same mode of delivery, and the duration of effect of single or multiple injections of cHyp. Six experimental protocols were used.

The first protocol studied whether cHyp delivered in liposomes was more effective than free cHyp in preventing pulmonary hypertension. Efficacy for each mode of drug delivery was determined as the minimal dose of cHyp required to prevent pulmonary hypertension after 3 days exposure to hypoxia. Free cHyp was given as 200 or 100 mg/kg subcutaneously twice daily (Groups 1 and 2). Free cHyp was also given as a single dose of 200 mg/kg intravenously prior to hypoxia (Group 3). Groups 1–3 were compared to groups exposed to air and hypoxia for 3 days and injected subcutaneously twice daily with saline. Groups 1 and 2 were also compared to groups given liposome-entrapped cHyp as a single intravenous injection of 200 or 100 mg/kg prior to exposure to hypoxia (Groups 4 and 5). Groups 4 and 5 were compared to a group exposed to hypoxia for 3 days and given a single intravenous injection of empty liposomes prior to hypoxia.

The second protocol studied the duration of antihypertensive effect of a single dose of 200 mg/kg cHyp entrapped in liposomes injected prior to exposure to hypoxia. Groups were studied after 3, 5 or 7 days of exposure to hypoxia (Groups 4, 6 and 7). Results were compared to age-matched air groups and groups injected with single doses of empty liposomes after 3, 5 or 7 days exposure to hypoxia.

The third protocol studied whether 200 mg/kg cHyp entrapped in liposome injected intravenously prior to and every 5 days during exposure to hypoxia prevented pulmonary hypertension on day 21 (Group 8). Results were compared to a group exposed to air for 21 days and to a group injected with empty liposomes prior to and every 5 days during a 21-day exposure to hypoxia.

The fourth protocol studied whether reticuloendothelial blockade prior to injection of cHyp entrapped in liposomes improved drug action. Reticuloendothelial blockade was produced by a single intravenous injection of empty liposomes (18 $\mu$mol phospholipid in 0.5 ml) 30 min. prior to the injection of cHyp in liposomes. Groups given 100 or 50 mg/kg cHyp intravenously after reticuloendothelial blockade (Groups 9 and 10) were compared to an air group and to a hypoxic group injected with 100 mg/kg cHyp without reticuloendothelial blockade (Group 5). Groups were compared at 3 days after exposure to hypoxia.

The fifth protocol compared the duration of effect of a single dose of 100 mg/kg cHyp entrapped in liposomes after reticuloendothelial blockade and studied at 3, 5 and 7 days of hypoxia (Groups 9, 11 and 12). Results were compared to an air group and to groups with reticuloendothelial blockade injected with single doses of empty liposomes and studied on days 3, 5 and 7 of hypoxia.

The sixth protocol studied whether cHyp injected in air breathing rats affected any of the parameters of exposure to hypoxia. Air groups were given free cHyp 200 or 100 mg/kg subcutaneously twice daily for 3 days (Groups 13 and 14) and were compared to saline injected animals. A group was injected with 200 mg/kg of cHyp in liposomes every 5 days during a 21-day exposure to air (Group 15), and results were compared to a group injected with empty liposomes every 5 days during a 21-day exposure to air.

Effect of Acute Injection of Liposomes on Right Ventricular Pressure

One group of anesthetized, catheterized, air-breathing rats was injected with a bolus of liposomes to determine the acute pressor effect of liposomes. After RVP was stable for 5–10 min., a bolus of empty liposomes (18 $\mu$mol phospholipid in 0.5 ml) was injected via the dorsal vein of the penis, and blood pressure was recorded continuously until it returned to baseline. The maximal increase in RVP during the first 2 min. after injection was compared to the blood pressure during the period prior to injection.

Uptake of Radiolabelled Liposomes by Pulmonary Artery Endothelial Cells in Culture Fresh bovine pulmonary arteries were perfused with sterile PBS containing 0.1 mg/ml gentamicin, 37° C., until free of blood. The endothelial cells were mechanically removed and placed in Medium 199 containing 10% fetal bovine serum, 5% calf serum, IU/ml penicillin, 100 $\mu$g/ml streptomycin, and 0.05 mg/ml gentamicin, pH 7.4, and not fed or moved for at least one week.

Thereafter, dividing cultures were fed twice weekly and passaged 7 times using a 2:1 split. Endothelial cells were identified by their characteristic cobblestone appearance in culture and the presence of angiotensin converting enzyme and factor VIII-related antigen by immunofluorescence. Endothelial cells ($1\times10^5$) and 100 $\mu$L of the above medium were added to each 38 mm$^2$ well of a 96-well flat bottom plate (Microtest II, Falcon Plastics, Oxnard, Calif.). Aliquots of liposomes containing [$^{14}$C]-L-proline (0.1 $\mu$Ci, 0.2 $\mu$mol phospholipid, 5 $\mu$l per well) were added to the cultured cells. Separate wells were used to measure uptake at intervals from 30 min. to 5 hr. After incubation, cells were washed 3 times with PBS, removed with 0.1 M sodium hydroxide, and radioactivity in a 500 $\mu$L aliquot counted in a liquid scintillation counter. The percent uptake of liposomes was estimated as the percentage of total radioactivity added per well.

Localization of Fluorescent Dye Entrapped in Liposomes in Pulmonary Artery Endothelial Cells in Culture To study whether liposomes are taken up by endothelial cells, liposomes (0.8 $\mu$mol phospholipid, 20 $\mu$l per well) containing the lipophilic fluorescent dye D282 were added to endothelial cells in culture for 0, 30 min., 1, 2, 3 and 5 hr. The cells were washed three times with medium and viewed using a microscope equipped with a fluorescence attachment. Endothelial cells with addition of empty liposomes were evaluated for autofluorescence.

Organ Distribution of Radiolabelled Liposomes

The distribution and retention of liposomes in selected organs was estimated by injecting radiolabelled liposomes in air-breathing mice and measuring radioactivity in the organs at times after injection. Mice were injected with [$^{14}$C]-L-proline in liposomes ($2.2\times10^5$ dpm in 100 $\mu$l) over one sec via the tail vein using a 30 g needle. Animals were killed by cervical dislocation at 1, 2, 6, 24, 48 and 72 hr. after injection. The lungs, heart, liver, spleen and kidneys were removed, rinsed in saline, blotted dry and weighed. A portion of each organ (100 mg) was solubilized in 2 ml methanol and quaternary ammonium hydroxide for 24 hr at 60° C. in a shaking water bath. A 100 $\mu$l aliquot of the suspension was added to 5 ml scintillation fluid (Econofluor, New England Nuclear Co., Boston, Mass.) and 2 ml methanol and quaternary ammonium hydroxide and counted in triplicate in a liquid scintillation counter. Counts were corrected for quenching by each tissue, and results were expressed as percent of total injected dose in each organ.

Statistical Analysis

Mean±SEM from each group were obtained. Data were analyzed by one-way ANOVA followed by Duncan's post-hoc test. Non-parametric data (animal survival) were analyzed by a continuity adjusted Chi-square analysis with Yates' correction. A P value of 0.05 was considered significant.

RESULTS

In General

Substantially lower doses of cHyp were effective in preventing pulmonary hypertension and collagen accumulation in pulmonary arteries when given intravenously in liposomes compared to subcutaneous administration of the free agent. Moreover, a single intravenous dose of cHyp entrapped in liposomes had a sustained effect on suppressing pulmonary hypertension. Delivery of an antifibrotic agent in liposomes improves drug action in the treatment of experimental pulmonary hypertension.

Animals

Survival was 128 of 130 (98%) in combined air groups and 165 of 192 (86%) in the combined hypoxic groups ($X^2$-5.8, $P<0.05$). Survival at 3 days of animals exposed to hypoxia and injected with saline or free cHyp was 13 of 16 (81%); survival of animals exposed to hypoxia and injected with liposomes was 51 of 61 (84%) (NS). After 3 days, 14 deaths occurred in the hypoxic group treated with liposomes (there were no age-matched saline or free cHyp treated animals exposed to hypoxia to compare survival). Initial body weight was 198±4 g (mean±SEM, n=322); final body weights were: day 3, 190–202 g; day 5, 204–208 g; day 7, 202–208 g; and day 21, 225–230 g. No differences were found on any day in final body weights among hypoxic animals treated with cHyp, hypoxic animals treated with the test substance, and air-breathing animals.

Hypoxia and Treatment with Empty Liposomes

Exposure to hypoxia from day 0 to day 21 produced progressive increases in all parameters in rats injected with empty liposomes; RVP increased from 9±1 to 21±2 mmHg, RV/(LV+S) from 0.24±0.01 to 0.43±0.02, hematocrit from 48±1 to 66±1%, hydroxyproline content from 74±4 to 163±14 µg/vessel and protein content from 1.2±0.1 to 3.2±0.3 mg/vessel (n=7–8, all $P<0.05$). All parameters were increased as early as 3 days exposure to hypoxia. The experimental data are illustrated in Table 4, further below.

Free vs. Liposome-Entrapped cHyp

The effect of free cHyp on preventing pulmonary hypertension at 3 days is demonstrated in the data shown in Table 4, further below. Treatment with 200 mg/kg cHyp subcutaneously twice daily for 3 days produced reductions in all 5 parameters compared to the saline injected hypoxic group. However, the values were greater than those in the air group, indicating that free cHyp partially prevented pulmonary hypertension. Injection of 100 mg/kg free cHyp subcutaneously for 3 days did not prevent increased RVP, RV/(LV+S) or hydroxyproline or protein contents; there was partial decrease in hematocrit (Table 4). Free cHyp injected intravenously prior to hypoxic exposure had no effect on any parameter (Table 4). A single dose of 200 mg/kg cHyp entrapped in liposomes injected prior to exposure to hypoxia partially prevented increases in RVP and hematocrit and completely prevented increases in RV/(LV+S) and contents of hydroxyproline and protein in pulmonary arteries at 3 days (FIG. 1). A single intravenous dose of 100 mg/kg cHyp entrapped in liposomes had no protective effect on any of the parameters at 3 days.

Duration of a Single Dose of cHyp Entrapped in Liposomes

A single intravenous injection of 200 mg/kg cHyp prior to exposure to hypoxia partially or completely prevented increases in RVP, RV/(LV+S) and hydroxyproline content of pulmonary artery at 3 and 5 days; increases in hematocrit and protein content were prevented at 3 days but not at 5 days (FIG. 1). At 7 days, a single injection of 200 mg/kg cHyp in liposomes did not prevent increases in any of the measured parameters (FIG. 1). Thus, a single intravenous injection of 200 mg/kg cHyp in liposomes prior to exposure to hypoxia partially suppressed the development of pulmonary hypertension, right ventricular hypertrophy and pulmonary artery collagen accumulation for 5 days.

Intermittent Doses of cHyp Entrapped in Liposomes

Intermittent injections of cHyp in liposomes every 5 days during the 21 day exposure period partially prevented the increases in RVP, RV/(LV+S) and hydroxyproline and protein contents of pulmonary artery; there was no effect on hematocrit (Table 5, further below). These results show that intermittent doses of single doses of cHyp in liposomes suppress the development of pulmonary hypertension for as long as three weeks.

Figure 3:
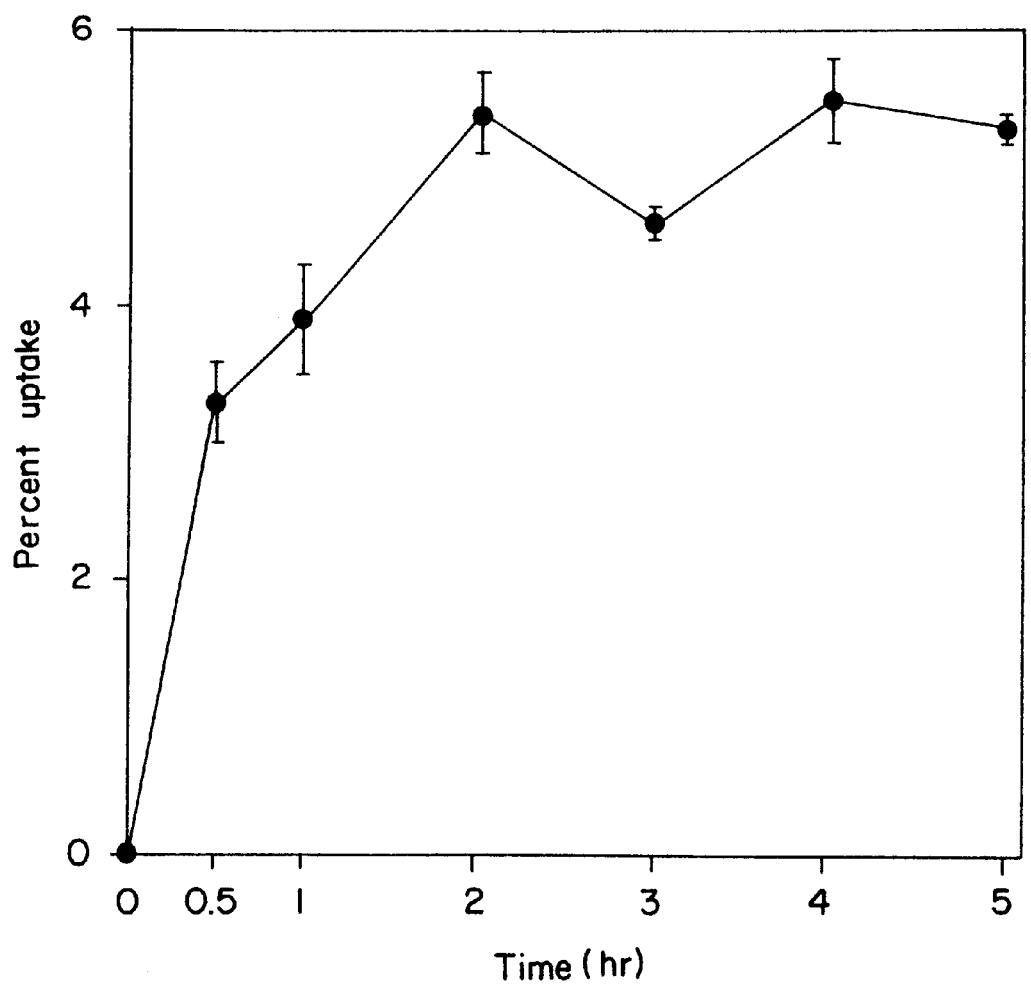
FIG. 3 is a graph depicting endothelial cell uptake of [$^{14}$C]-L-proline entrapped in liposomes. Data points, mean; bracket, ±SE; n=4. Time, time of study; percent, percent uptake of radiolabelled liposomes by cultured pulmonary artery endothelial cells.

Single Dose of cHyp Entrapped in Liposomes after Reticuloendothelial Blockade In animals with reticuloendothelial blockade, a single dose of 100 mg/kg cHyp entrapped in liposomes partially prevented the increases in RVP, RV/(LV+S) and hydroxyproline content of the pulmonary artery at 3 days; there was no apparent effect on hematocrit and protein content of pulmonary artery at 3 days (FIG. 2). A dose of 50 mg/kg had no protective effect on any parameter at 3 days (FIG. 3). Since the minimal effective dose of cHyp in liposomes without reticuloendothelial blockade was 200 mg/kg, these results suggest that reticuloendothelial blockade prior to a single dose of cHyp in liposomes results in a lower effective dose of cHyp.

Duration of a Single Dose of cHyp Entrapped in Liposomes after Reticuloendothelial Blockade In animals with reticuloendothelial blockade, treatment with a single intravenous injection of 100 mg/kg prior to exposure to hypoxia partially or completely prevented increases in RVP, RV/(LV+S) and hydroxyproline content of the pulmonary artery at 3 and 5 days; there was no effect on hematocrit or protein content (FIG. 2). At 7 days after a single injection, the agent did not prevent increases in any of the measured parameters (FIG. 2). The pattern of suppression was similar to that found without reticuloendothelial blockade (FIG. 1), except the dose was 100 mg/kg instead of 200 mg/kg.

cHyp in Air-Breathing Rats

There was no effect of 200 mg/kg or 100 mg/kg cHyp injected twice daily subcutaneously for 3 days on any of the measured parameters (Table 4). Also, intermittent intravenous injections of 200 mg/kg cHyp in liposomes every 5 days during a 21-day air exposure period had no effect on any parameter (Table 5).

Effect of Injection of Liposomes on Right Ventricular Pressure

Mean right ventricular pressure increased from 9±1 to 11±1 (mmHg) (n=5) within 2 min after injection of cHyp entrapped in liposomes ($P<0.05$). Injection of saline under the same conditions had no effect on RVP (9±1 vs. 10±1 mmHg, n=4).

Uptake of Liposomes by Endothelial Cell in Culture

Percent uptake of liposome containing [$^{14}$C]-L-proline by pulmonary artery endothelial cells was 3.3±0.3% at 30 min. Uptake was maximal at 5.4±0.3% after 2 hr and remained at that level for 5 hr (FIG. 3).

Localization of Fluorescent Dye Entrapped in Liposomes

Figure 4:
FIG. 4 shows the localization of fluorescent dye entrapped in liposomes in cultured pulmonary artery endothelial cells. Diffuse uptake of fluorescent dye by endothelial cells. Inset, fluorescence of cells with empty liposomes.

At 30 min after incubation with the fluorescent dye D282, a diffuse pattern of immunofluorescence was observed in endothelial cell membranes (FIG. 4). At 2 hr a few fluorescent intracellular vesicles appeared which became more abundant at 3 to 5 hr after incubation. Autofluorescence was absent in cells not incubated with D282.

Organ Distribution of Radiolabelled Liposomes

Figure 5:
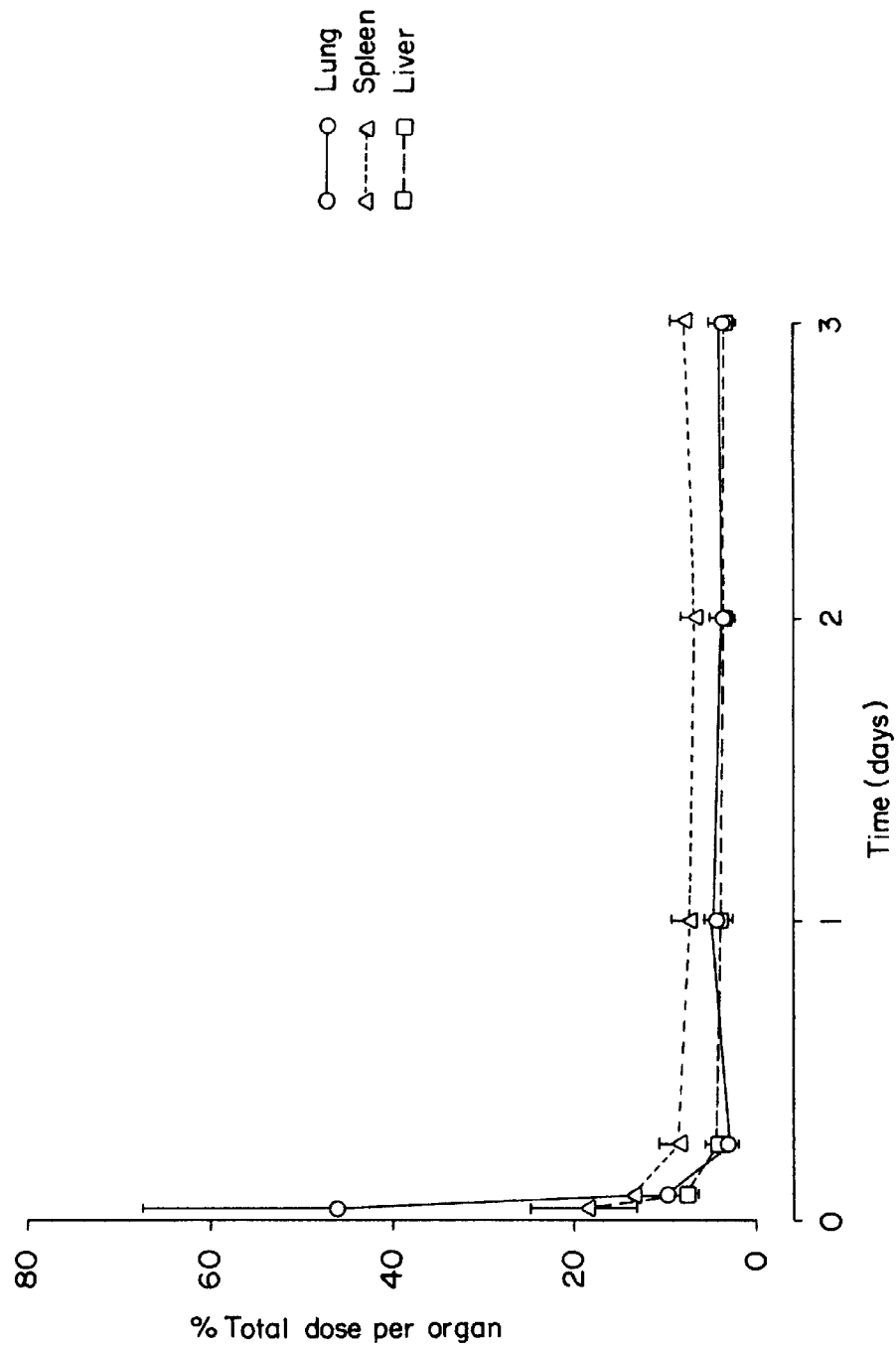
FIG. 5 is a graph depicting the uptake of [$^{14}$C]-L-proline in liposomes in selected organs. The % total injected dose of [$^{14}$C]-L-proline (ordinate) vs. time after injection (abscissa). Data points, mean; bracket, ±SE, n=4.

Soon after administration of [$^{14}$C]-L-proline entrapped in liposomes, radioactivity appeared in the lung where it reached a maximum of 49±14% of total injected dose during the first 20 min (FIG. 5). There was a rapid decrease in lung activity reaching a value of 5±1% at 6 hr. Spleen took up a greater proportion of radioactivity (9±1% at 6 hr) and retained—7–9% for up to 72 hr. Liver retained about the same amount as lung; heart and kidney contained <2% activity after 6 hr (not shown). After 72 hr, the lung contained 5±1% of total activity (FIG. 5).

DISCUSSION

The examples above demonstrate that the intravenous injection of cHyp in liposomes partially prevents the development of pulmonary hypertension in rats exposed to hypoxia. Liposome entrapment was necessary for drug action since intravenous injection of free cHyp was ineffective. Compared to subcutaneous administration, intravenous delivery of cHyp in liposomes required considerably less total dose of drug to prevent hypertension. Moreover, delivery of cHyp in liposomes resulted in sustained drug effect; pulmonary hypertension was suppressed for 5 days after a single intravenous injection of cHyp in liposomes. This effect could be extended for as long as three weeks by a single injection every 5 days. Drug action on the pulmonary circulation could be improved by blocking uptake by reticuloendothelial organs prior to delivering the agent. cHyp was chosen to test the effect of liposome delivery of drugs to blood vessels because it consistently prevents the early hemodynamic and biochemical changes of hypoxic pulmonary hypertension in the rat. The minimal total dose of cHyp required to prevent hypoxic pulmonary hypertension using different modes of delivery was compared.

At 5 days the results were as follows: subcutaneous, 2000 mg/kg (200 mg/kg twice daily); single dose entrapped in liposomes without reticuloendothelial blockade, 200 mg/kg; single dose entrapped in liposomes with reticuloendothelial blockade, 100 mg/kg. Over the 5-day interval, the dose using cHyp entrapped in liposomes following reticuloendothelial blockade was approximately 20 times more effective than a subcutaneous dose of free cHyp.

The assumption is made that cHyp is released from liposomes in the vicinity of vascular cells synthesizing collagen, thereby preventing accumulation of collagen. There are two general pathways which liposomes might follow to enter the blood vessel wall. First, liposomes injected intravenously may be taken up by pulmonary vascular endothelial cells. Liposomes pass easily into reticuloendothelial organs because the endothelium of these organs is fenestrated. In organs with tight endothelium, such as lung, liposomes remain associated with endothelial surfaces until they are degraded or endocytosed. Although it was shown that liposomes are taken up by endothelial cells in vitro, there is no evidence that this process occurred in vivo. Second, liposomes may be taken up by circulating blood phagocytes and migrate into the lung tissue. Blood monocytes phagocytose liposomes and subsequently migrate to the alveoli to become alveolar macrophages. The analogue may be released from blood cells as they pass through the blood vessel walls. Liposomes are also phagocytosed by pulmonary intravascular macrophages, but the rat has few if any of these cells. Either of these two pathways may be involved in release of cHyp to blood vessel walls.

These biochemical mechanisms probably account for the decreased accumulation of collagen in pulmonary arteries in the Examples. In addition, collagen synthesis in the main pulmonary arteries of rats is markedly increased within 3 days of exposure to hypoxia and remains elevated for 7 days. Collagen synthesis is increased only in the pulmonary artery, probably because hypoxia causes structural remodeling in response to hypoxic hypertension in the pulmonary circulation. Proline analogues impair collagen formation in tissues undergoing increased collagen synthesis, such as the pulmonary artery in early hypoxic pulmonary hypertension.

Treatment with cHyp is relatively specific for inhibiting collagen synthesis. For example, doses of cHyp which inhibit collagen accumulation do not affect elastin accumulation. Nevertheless, it was observed that treatment with cHyp prevented increases in total protein accumulation at 3 days. Suppression of protein accumulation cannot be accounted for by the decreased collagen since collagen synthesis contributes only about 4–5% of the total protein synthesis in hypertensive pulmonary arteries of rats. One explanation is that cHyp may have interfered with the ability of vascular smooth muscle cells and fibroblasts to proliferate, since cHyp inhibits proliferation of cultured cells by blocking collagen secretion required for cells to attach and grow. Marked cell proliferation occurs in hilar pulmonary arteries of rats 2–3 days after onset of hypoxia, and suppression of this proliferation by cHyp may explain why protein content was suppressed is early hypertension. At 5 days and later, there is little cell proliferation and cHyp has no effect on protein accumulation after 3 days.

Hypoxia-induced polycythemia was inhibited by the higher doses of cHyp, an effect previously noted with subcutaneous injection of cHyp.

The rate of rise of right ventricular pressure and hydroxyproline content were similar between 0 and 3 days in the hypoxic group and between 5 and 7 days in the hypoxic groups given a single injection of cHyp in liposomes (FIGS. 1 and 2). It was speculated that the suppressive effect of cHyp in liposomes diminished after 5 days, and collagen accumulated rapidly in the blood vessel wall. The late increase in collagen may have contributed to narrowing of the vascular lumen producing hypertension. The stimulus for rapid collagen accumulation at flow-resistive sites, presumably hypoxic vasoconstriction, persisted during hypoxia, but the added effect of collagen accumulation occurred only after the drug effect wore off.

It is possible to enhance the delivery of liposomes to the lung by blockade of the reticuloendothelial organs. With blockade, half as much cHyp is required in liposomes to prevent the rise in pulmonary blood pressure as without RES blockade, suggesting that blockade produced a shift toward a greater portion of injected liposomes to the lung.

Intravenously injected liposomes will be initially distributed to lungs since it is the first organ they contact. Thereafter, liposomes are distributed to other organs or are excreted. A small fraction of the total radioactivity (4–5%) remains in the lung for as long as 3 days, incorporated into tissue protein or retained in liposomes. These findings are consistent with the observation that cHyp within the lung is available to inhibit collagen accumulation for up to 5 days after intravenous injection.

In conclusion, the results show that intravenous injection of an agent entrapped in liposomes substantially improves the action of an agent which inhibits the development of hypertension, probably by delivering a locally high concentration of drug which is released over time within the blood vessel wall. The encapsulated agent given intravenously was approximately 20 times more effective than the unencapsulated agent given subcutaneously.

Tables 3–5 are set out immediately below. Table 3 contains data concerning the protocols which were used and the experimental groups involved. Table 4 contains data on the effects of injecting free cHyp on various hemodynamic and biochemical measurements. Table 5 contains data on the effects of injections of liposomal cHyp on various hemodynamic and biochemical measurements.

TABLE 3

EXPERIMENTAL GROUPS

| Mode of Delivery of cHyp | Route | Dose (mg/kg) | Frequency of Injection Exposure to Hypoxia | Duration of Exposure (days) | Group Number |
|---|---|---|---|---|---|
| Free | sc | 200 | Twice daily during hypoxia | 3 | 1 |
|  | sc | 100 | Twice daily during hypoxia | 3 | 2 |
|  | iv | 200 | Single dose prior to hypoxia | 3 | 3 |
| Liposomes, single doses | iv | 200 | Single dose prior to hypoxia | 3 | 4 |
|  | iv | 100 | Single dose prior to hypoxia | 3 | 5 |
|  | iv | 200 | Single dose prior to hypoxia | 5 | 6 |
|  | iv | 200 | Single dose prior to hypoxia | 7 | 7 |
| Liposomes, intermittent doses | iv | 200 | Prior to hypoxia and every 5 days during hypoxia | 21 | 8 |
| Liposomes, single doses, reticuloendothelial blockade | iv | 100 | Empty liposomes followed by 30' later by single dose prior to hypoxia | 3 | 9 |
|  |  | 50 |  | 3 | 10 |
|  | iv | 100 |  | 5 | 11 |
|  | iv | 100 |  | 7 | 12 |
|  |  |  | Exposure to Air |  |  |
| Free | sc | 200 | Exposure twice daily during air | 3 | 13 |
|  | sc | 100 |  | 3 | 14 |
| Liposomes, single doses | iv | 200 | Every 5 days during exposure | 21 | 15 |

Abbreviations: cHyp, cis-4-hydroxy-L-proline; free, cHyp not contained in liposomes; liposomes, cHyp entrapped in liposomes; sc, subcutaneous; iv, intravenous

TABLE 4

EFFECTS OF INJECTION OF FREE cHyp ON HEMODYNAMIC AND BIOCHEMICAL MEASUREMENTS ON DAY 3

| Exposure/ Regimen | n | RVP (mm Hg) | RV/(LV + S) (%) | Hct (%) | Hydroxyproline (mg/vessel) | Protein (mg/vessel) |
|---|---|---|---|---|---|---|
| Air, saline | 6 | 9 ± 1 | 0.24 ± 0.01 | 48 ± 1 | 75 ± 4 | 1.2 ± 0.1 |
| Hypoxia, saline | 8 | 14 ± 1* | 0.30 ± 0.01* | 54 ± 1* | 90 ± 2* | 1.7 ± 0.1* |
| Hypoxia, free cHyp |  |  |  |  |  |  |
| 200 mg/kg sq bid × 3 days | 10 | 10 ± 1** | 0.25 ± 0.01** | 51 ± 1** | 78 ± 4** | 1.4 ± 0.1** |
| 100 mg/kg sq bid × 3 days | 5 | 14 ± 1 | 0.31 ± 0.02* | 51 ± 1** | 94 ± 4 | 2.3 ± 0.3* |
| 200 mg/kg iv × 1 injection | 9 | 14 ± 1* | 0.32 ± 0.01* | 55 ± 1* | 88 ± 7* | 2.3 ± 0.3* |
| Air, free cHyp |  |  |  |  |  |  |
| 200 mg/kg sq bid × 3 days | 6 | 9 ± 1 | 0.24 ± 0.01 | 46 ± 1 | 72 ± 5 | 1.2 ± 0.1 |
| 100 mg/kg sq bid × 3 days | 4 | 9 ± 1 | 0.25 ± 0.01 | 47 ± 1 | 70 ± 2 | 1.2 ± 0.1 |

Values, mean ± SEM. Measurements taken 3 day after exposure to air on 10% $O_2$. n = number animals/group.
Abbreviations: cHyp, cis-4-hydroxy-L-proline; iv, intravenous; sq, subcutaneous; bid, twice daily; RVP, mean right ventricular pressure; RV/(LV + S), ratio of ventricular weights; Hct, hematocrit; *, P < 0.05 compared with air; **P < 0.05 compared with hypoxia.

TABLE 5

EFFECTS OF INTERMITTENT INJECTIONS OF cHyp IN LIPOSOMES ON HEMODYNAMIC AND BIOCHEMICAL MEASUREMENTS ON DAY 21

| Exposure/Regimen | n | RVP (mm Hg) | RV/(LV + S) (%) | Hct (%) | Hydroxyproline (mg/vessel) | Protein (mg/vessel) |
|---|---|---|---|---|---|---|
| Air, empty liposome | 8 | 9 ± 1 | 0.24 ± 0.01 | 47 ± 2 | 79 ± 6 | 1.5 ± 0.1 |
| Air, liposomes, cHyp | 8 | 9 ± 1* | 0.24 ± 0.01 | 46 ± 1 | 84 ± 3 | 1.4 ± 0.2 |
| Hypoxia, empty | 7 | 21 ± 2* | 0.43 ± 0.02* | 66 ± 1** | 163 ± 14* | 3.2 ± 0.3* |
| Hypoxia, liposomes, cHyp | 7 | 15 ± 1** | 0.36 ± 0.01** | 68 ± 1* | 121 ± 12** | 2.4 ± 0.2** |

Values, mean ± SEM. Measurements taken 3 day after exposure to air on 10% $O_2$. n = number animals/group.
Abbreviations: cHyp, cis-4-hydroxy-L-proline; iv, intravenous; sq, subcutaneous; bid, twice daily; RVP, mean right ventricular pressure; RV/(LV + S), ratio of ventricular weights; Hct, hematocrit; *, $P < 0.05$ compared with air; **$P < 0.05$ compared with hypoxia.

EXAMPLE 17

Synthesis and Characterization of Poly(PEG-Lys-cHyp) Copolymers

All precursor and final compounds were fully characterized by $^1$H and $^{13}$C NMR, elemental analysis, gel permeation chromatography (GPC), and scintillation counting, as appropriate.

Preparation of Lys-cHyp 2HCl

L-Lysine-cis-4-hydrochloride (Lys-cHyp 2HCl) was prepared by cHyp coupling to Nα,Nε-di-t-butoxycarbonyl-L-lysine N-hydroxysuccinimide ester followed by HCl deprotection. $^{13}$C NMR ($D_2O$, ppm): 23.6 (γ-$CH_2$ of Lys), 29.3 (δ-$CH_2$ of Lys), 32.4 (β-$CH_2$ of Lys), 39.2 (β$CH_2$ of Hyp), 42.0 (ε-$CH_2$ of Lys), 54.4 (δ-$CH_2$ of Hyp), 57.5 (α-CH of Lys), 61.0 (α-CH of Hyp), 72.6 (γ-CH of Hyp), 171.7 (C=O of amide), 177.6 (C=O of Hyp). $[α]^{25}_D$=−20.9° (c=1, $H_2O$). Amino acid analysis (molar ratio): Lys/cHyp: 0.98/1.00. Elemental Lys-cHyp+3HCl+3$H_2O$ (theo): %C 31.09 (31.25); %H, 6.25 (7.15); %N, 9.64 (9.94); %Cl, 24.98 (25.16).

The procedures followed for the synthesis of Lys-tHyp 2HCl were the same as for the preparation of the cHyp derivative described above, with the exception that cHyp was replaced with tHyp.

The synthesis of the dual radiolabeled dipeptide required the di-t-butyloxycarbonyl protection of [$^{14}$C]-L-lysine, in accordance with the procedures described in Ponnusamy et al., *Synthesis*, 1986, 48–49; NHS activation in accordance with the procedures described in Ogura et al., *Tetra. Lett.*, 1979, 49:4745–4746; and subsequent coupling of [$^3$H]cHyp followed by deprotection.

Preparation of BSC-PEG

Bis(succinimidyl) poly(ethylene glycol) (BSC-PEG) was prepared as described in Nathan et al., *Macromolecules*, 1992, 25:4476–4484.

Preparation of poly(PEG-Lys-Hyp)

The drug containing copolymers were prepared by dissolving 7.0 g (3.1 mmol) of BSC-PEG and 1.0 g (3.1 mmol) of Lys-Hyp 2HCl in 15 mL of water. Stirring was continued for an additional 6 hrs and the solution was adjusted to pH 2 (conc. HCl), and the product extracted immediately with several portions of methylene chloride. The solution was dried over anhydrous $MgSO_4$, filtered and concentrated to dryness. The poly(PEG-Lys-Hyp) conjugates were generally isolated at >98% yields. For the unlabeled materials, the degree of Hyp attachment was determined by amino acid analysis and the molecular weights determined by GPC.

Data on the amide-linked Hyp conjugates were as follows: A) poly(PEG-Lys-cHyp): Lys/cHyp: 1.00/0.98 and Mw=21.6×10$_3$ g/mol (Mw/Mn=1.52), and B) poly(PEG-Lys-tHyp): Lys/cHyp: 0.64/0.36 and Mw=46.5×10$_3$ g/mol (Mw/Mn=2.11). The dual labeled material had an Mw=31.2×10$^3$ (Mw/Mn=1.91) and a specific activity as follows: [$^{14}$C] 4.04×10$^4$ dpm/mg; [$^3$H]3.63×10$^4$ dpm/mg. $^{13}$C NMR ($D_2O$, ppm) of the poly(PEG-Lys-cHyp): 25.2 (γ$CH_2$ of Lys), 31.5 (δ-$CH_2$ of Lys), 34.5 (β-$CH_2$ of Lys), 39.5 (β-$CH_2$ of Hyp), 43.2 (ε-$CH_2$ of Lys), 55.8 (α-CH of Lys), 57.6 (δ-$CH_2$ of Hyp), 59.6 (α-CH of Hyp), 63.4–72.6 (PEG), 74.8 (γ-CH of Hyp), 160.8 (E-C=O of NH urethane), 161.4 (α-C=O of NH urethane), 175.7 (α-C=O of amide), 182.1 (C=O of Hyp). [$^{13}$C NMR ($CDCl_3$, ppm) of the poly(PEG-Lys-cHyp): 21.6 (γ$CH_2$ of Lys), 29.2 (δ-$CH_2$ of Lys), 31.9 (β-$CH_2$ of Lys), 36.7 (β-$CH_2$ of Hyp), 40.4 (ε-$CH_2$ of Lys), 51.9 (4-CH of Lys), 55.5 (δ-$CH_2$ of Hyp), 57.4 (α-CH of Hyp), 61.6–70.4 (PEG+γ-CH of Hyp), 155.8 (ε-C=O of NH urethane), 156.5 (α-C=O of NH urethane), 171.2 (α-C=O of amide), 173.3 (C=O of Hyp)].

EXAMPLE 18

Synthesis and Characterization of Liposomal Poly (PEG-Lys-Hyp)

Liposome Preparation and Characterization

A cholesterol derivatized amylopectin was prepared to serve as a coating for PEG-conjugated liposomes. The derivitization of amylopectin with cholestryl residues was carried out in accordance with the procedure of Sunamoto; Sato et al., *Liposome Technology*, 2nd Ed., Boca Raton: CRC, 1993: 180–198, Vol.3; Sato and Sunamota, *Prog. Lipid Res.*, 1992, 31:345–372; Sunamoto et al., *Biochimica et Biophysica Acta*, 1987, 898:323–330. Amylopectin was carboxymethylated with sodium monochloroacetate (CAA) followed by coupling of ethylenediamine (ED) using 1-(3-dimethylaminopropyl)-3-ethylcarbodiimide. Cholesterol (CHOL) derivatization was accomplished by adding dimethylformamide in solution with cholesteryl chloroformate. The derivatized polysaccharide was isolated as a fine, light tan powder. The degree of attachment to the amylopectin was determined by $^1$H NMR in $D^2O$ (CAA and ED) and $d_6$-DMSO (Chol): CAA 28%; ED 8%; Chol 2%.

PEG-conjugated liposomes (PEG-lipo) were prepared in accordance with the procedures described in Poiani et al., Amino Acids, 1993, 4:237–248; and small, unilamellar liposomes were prepared in accordance with the procedures described in Poiani et al., Circ. Res., 1992, 70:912–922, and characterized as previously described. The unilamellar liposomes were coated with cholesterol derivatized amylopectin (CHA) by incubating at 20° C. for 1 hr at a ratio of 0.2:1 (w/w) CHA:total lipid, with gentle stirring (CHA-lipo). Unbound polysaccharide was removed by centrifugation. All liposomes were prepared and stored under a nitrogen atmosphere. The diameters of 90% of the liposomes, measured by a fluorescent activated cell sorter using latex beads as standards, using the method described in Poiani, 1992, were 240±30 nm for PEG-lipo and 300±30 nm for CHA-lipo (n=5–6). Entrapment, measured as the percentage of poly (PEG-[$^{14}$C]Lys-[$^3$H]cHyp) sequestered in liposomes, was 46±4% for PEG-lipo (n=6) and 45±3% for CHA-lipo (n=5). Stability of entrapment during storage, measured for 21 days at 4° C., was unchanged. CHA-coated liposomes retained their lectin binding properties during storage, since aggregation following incubation with Concanavolin-A, in accordance with the procedure described in Iwamoto et al., J. Pharmaceut. Sci., 1991, 80:219–224, did not change.

Organ Retention of [$^3$H]cHyp and Poly (PEG-[14C] Lys Carrier

Six week-old male Sprague-Dawley rats (Crl:CD[SD] BR) weighing 180–200 g, were obtained from Charles River Laboratories, Wilmington, Mass. The animals were maintained for 1 week prior to study and fed rodent chow and water ad libitum. Four groups of rats (n=5) were anesthetized (ketamine, 75 mg/kg and xylazine 5 mg/kg, i.p.) and injected via the dorsal vein with 1 mL dual labeled poly (PEG-[$^{14}$C]Lys-[3H]cHyp) (12.5 mg/ml) in CHA-lipo or in PEG-lipo (40 μmol phospholipid). To assess organ retention, radioactivity in lung, liver, spleen and blood was measured at 6 hr and 7 days (Table 6) in accordance with the method described in Poiani et al., Am. J. Respir. Crit. Care Med., 1994, 150:1623–1627. The results are set out in Table 6, immediately below.

TABLE 6

Percent Biodistribution[1] of Remaining Dose of [$^3$H]cHyp in Selected Organs Delivered by Liposomes Containing poly(PEG-[$^{14}$C]Lys-[$^3$H]cHyp)

| Tissue | 6 Hours PEG-Lipo | 6 Hours CHA-Lipo | 7 Days PEG-Lipo | 7 Days CHA-Lipo |
|---|---|---|---|---|
| Lung | 7.5 ± 0.5 | 10.6 ± 0.5[2] | 2.7 ± 0.2[3] | 5.2 ± 0.8[2,3] |
| Blood | 43.1 ± 8.2 | 50.8 ± 10.4 | 3.4 ± 2.1[3] | 25.9 ± 9.4[2] |
| Liver | 23.4 ± 3.1 | 29.4 ± 4.1 | 15.6 ± 2.5 | 26.5 ± 3.0[2] |
| Spleen | 70.5 ± 1.0 | 20.0 ± 1.2[2] | 45.5 ± 3.4[3] | 29.5 ± 3.8[2] |

[1]Values are the mean ± SEM for n = 5 per group. Values are a % of the total injected [$^3$H] per g weight of tissue at 6 hours and 7 days after a single i.v. injection of poly(PEG-[$^{14}$C]Lys-[$^3$H]cHyp) in PEG-liposome vehicle or CHA-liposome vehicle, as determined in the protosol/liquiscint (1/5 v/v).
[2]p < 0.05 compared with the PEG-liposome vehicle group in the corresponding time column.
[3]p < 0.05 compared with the corresponding 6 hours group.

Counts were corrected for weight of the whole organ or plasma volume using the method described in Wang, Am. J. Physiol., 1959, 196:188–192. Data were expressed as a percentage of the injected radioactivity recovered per gram of tissue or per mL of blood. To compare stability of the conjugate in PEG-lipo and CHA-lipo, the dpm ratio of [$^3$H] to [$^{14}$C] was measured in tissues in accordance with the method described in Jurima-Romet et al., Int. J. Pharmaceutics, 1990, 63:227–235. The results are shown in Table 7 immediately below.

TABLE 7

[$^3$H]/[$^{14}$C] Ratios in Selected Tissues[1]

| Tissue | 6 Hours PEG-Lipo | 6 Hours CHA-Lipo | 7 Days PEG-Lipo | 7 Days CHA-Lipo |
|---|---|---|---|---|
| Lung | 18.0 ± 7.3[2] | 13.0 ± 1.3[2] | 33.0 ± 9.4[2] | 17.0 ± 3.1[2] |
| Blood | 16.0 ± 5.4[2] | 32.0 ± 10.7[2] | 65.0 ± 21.2[2] | 140.0 ± 35.2[2] |
| Liver | 5.0 ± 1.2[2] | 9.0 ± 1.6[2] | 7.0 ± 1.1[2] | 22.0 ± 3.2[2] |
| Spleen | 3.0 ± 0.5 | 5.0 ± 0.7 | 6.0 ± 1.0 | 22.0 ± 1.4 |

[1]Values are the mean ± SEM for n = 5 per group. Data consists of ratios of dpm [$^3$H] to [$^{14}$C] in liposome vehicles in solubilized tissues at 6 hours and 7 days following i.v. injection.
[2]p < 0.05 compared to the liposome matched preinjection ratio.

C-Hyp Release Studies in Various pH Buffers and Bovine Calf Serum

Buffers at various pH levels were prepared according to the method described in Davies, The Analyst, 1959, 4:248–251, with final ionic strengths of approximately 0.15 mol/L. Incubation samples were prepared by dissolving the dual-labeled conjugate in the appropriate medium to obtain a 50 mg/mL concentration and immediately syringe filtering through 0.45 μm nylon filters. Aliquots (25–30 μL) at specified time points were removed for GPC analysis-fractionation. Release rates were determined by monitoring cleavage of the radiolabeled [$^3$H]-cHyp from the radiolabeled [$^{14}$C] polymeric backbone. Separation of the relatively high molecular weight backbone from the low molecular weight drug was readily achieved via gel permeation chromatography, which is a size separation technique, followed by scintillation counting of the collected fractions. This necessitated using radiolabeled-conjugate concentrations of 50 mg/mL, i.e., 1 mg of conjugate injected per run, resulting in appropriate molecular weight analysis and specific activity determinations for the collected fractions. The serum release studies were conducted in 100% heat inactivated fetal calf serum (ΔFCS) at 37° C. at a concentration of 50 mg/mL of conjugate to ΔFCS, over a six day period.

Design Aspects Relating to the Conjugate Poly (PEG-Lys-Hyp)

Figure 10:
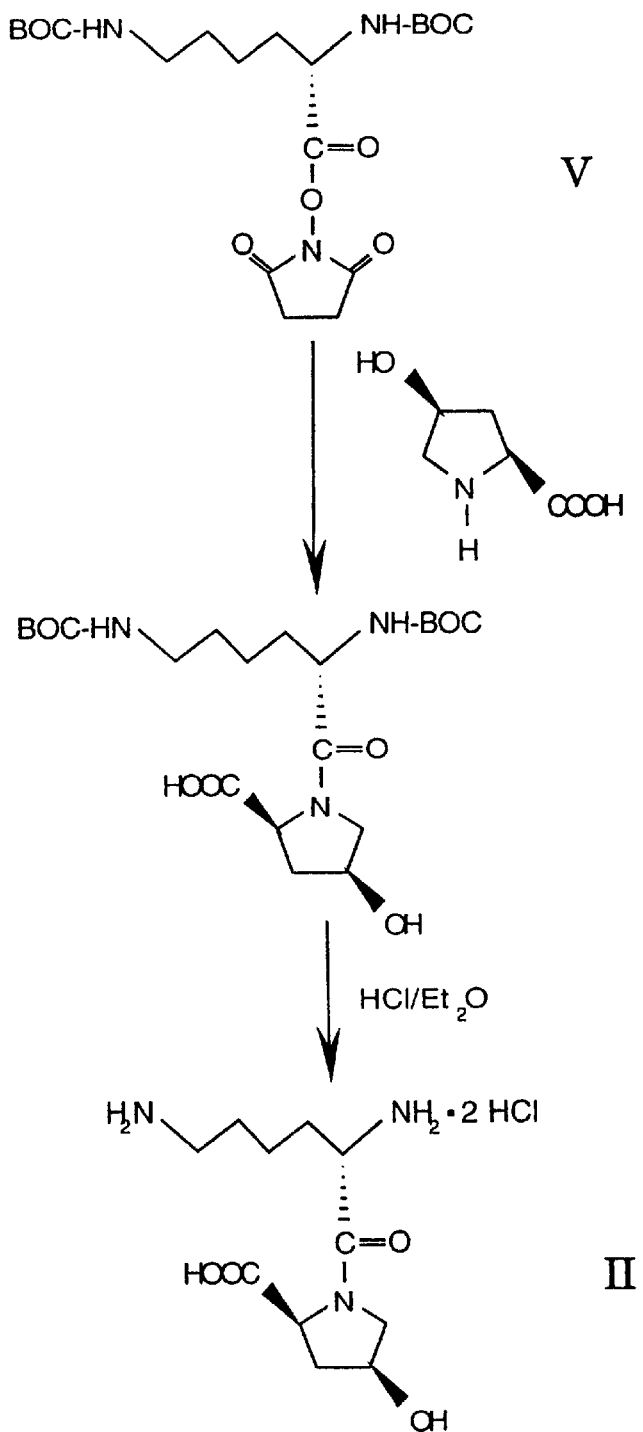
Figure 11:
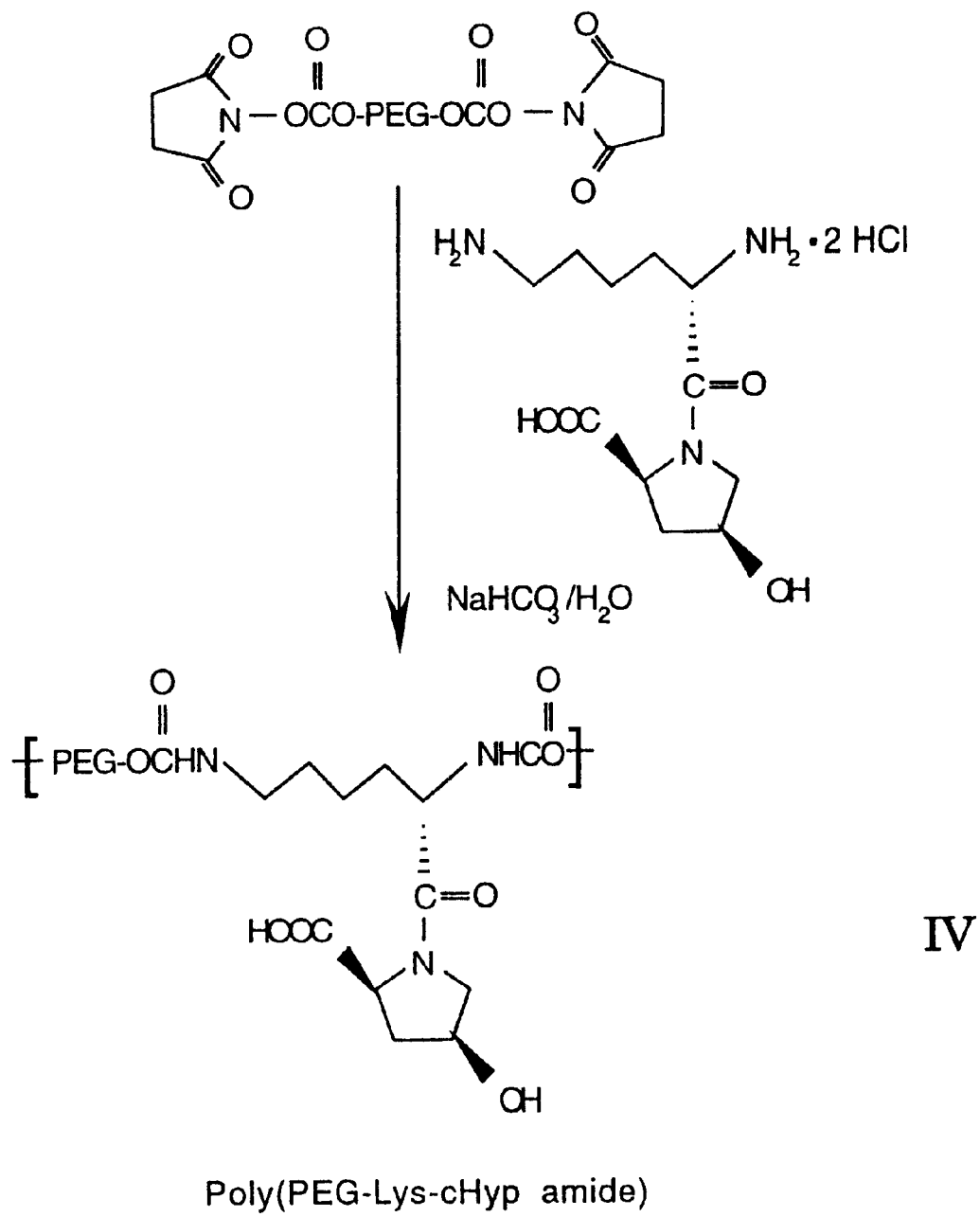
FIG. 11 is a depiction of the synthetic scheme for the copolymerization of Lys-cHyp with BSC-PEG, and is also identified as Scheme 1: Step b.
Figure 12A:
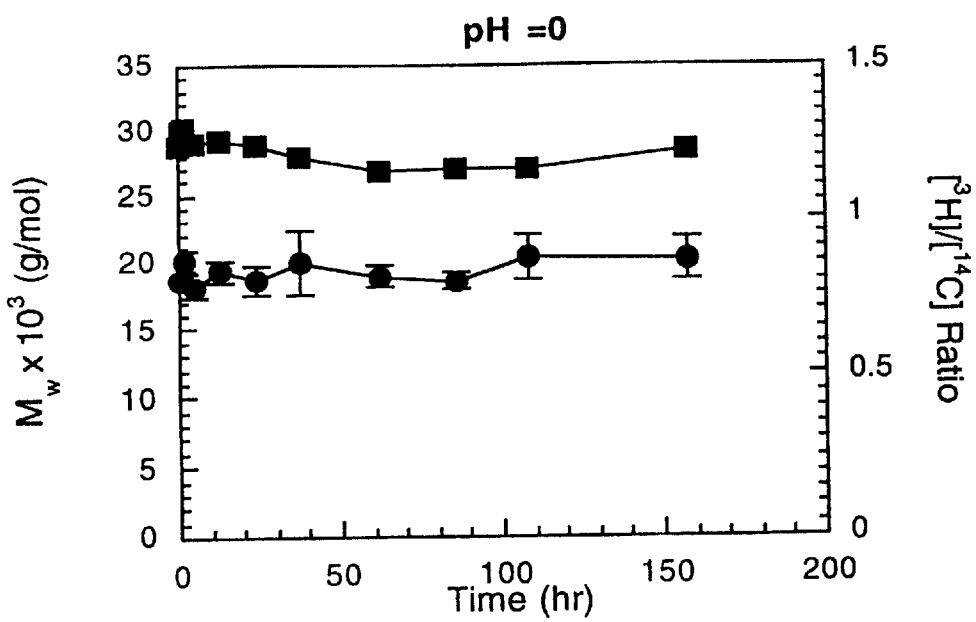
FIG. 12 is in five parts, a)–d), which are graphs showing molecular weight as $M_w$ or weight average molecular weight, and incorporated dipeptide stability profiles of the poly(PEG-[$^{14}$C]Lys-[$^3$H]cHyp) at 25° C at a) pH=0, b) p=7, c) p=14, and d) 100% FCS. In the graphs, ■=$M_w$ profile, and ●=[$^3$H]/[$^{14}$C] profile.
Figure 12B:
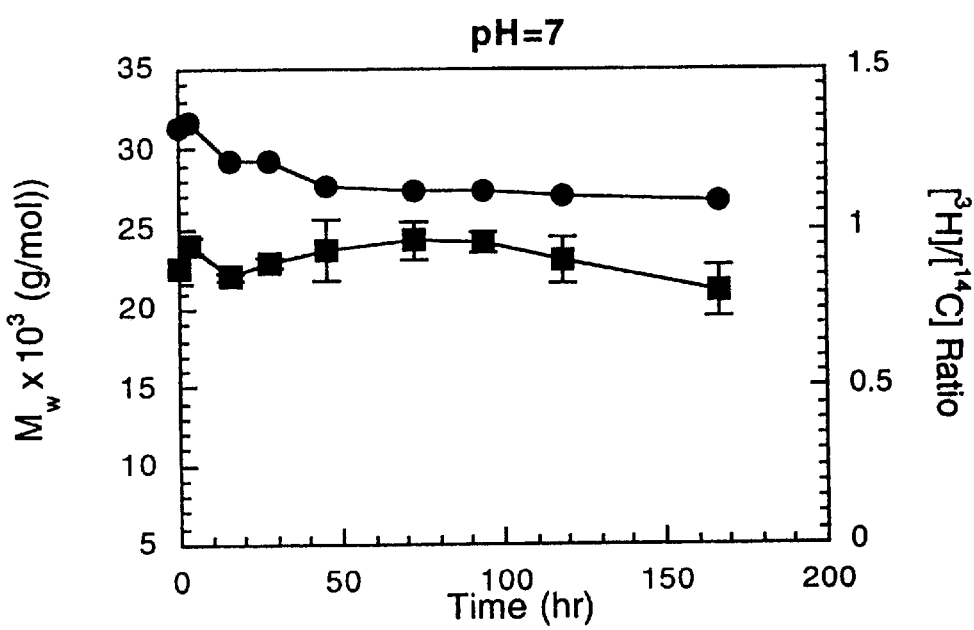
Figure 12C:
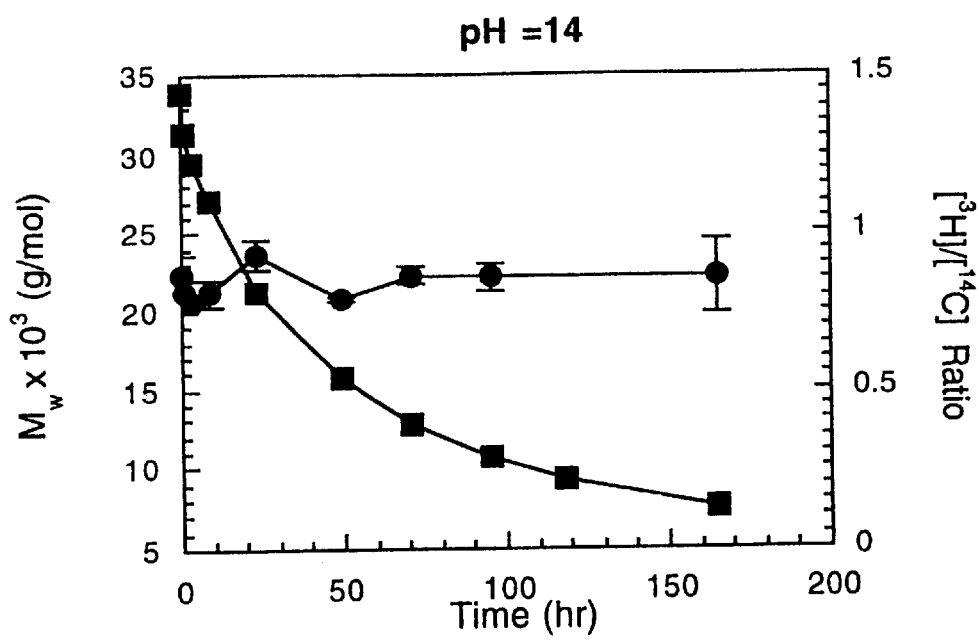
Figure 12D:
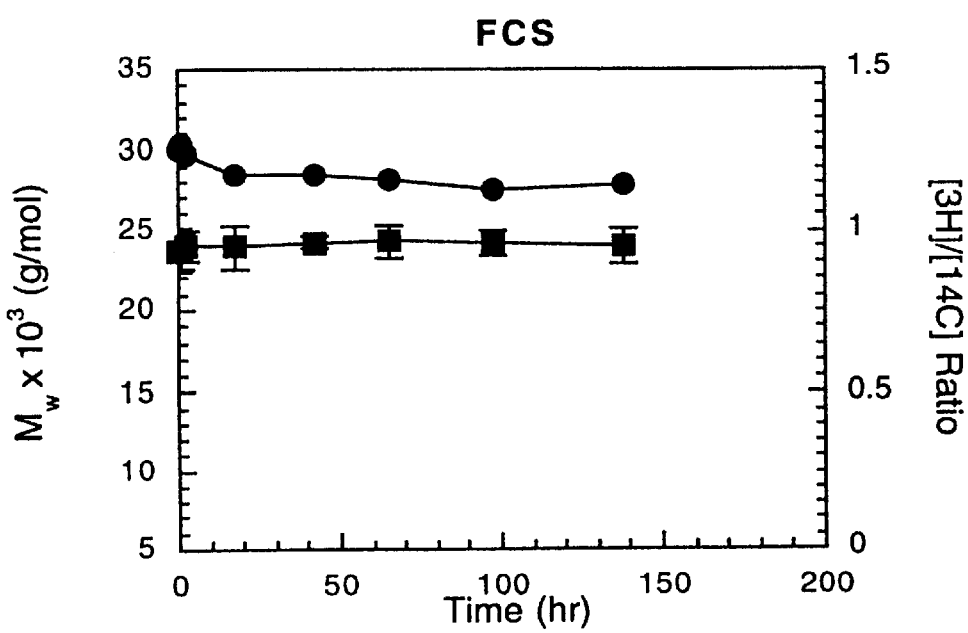
Figure 13:
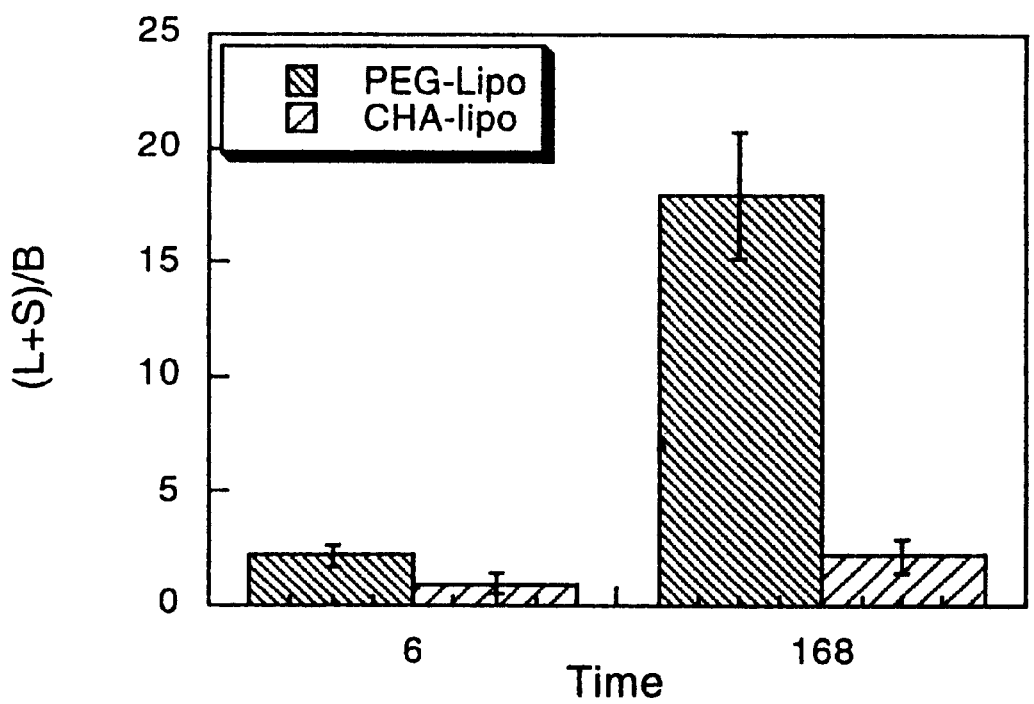
FIG. 13 depicts a graphical evaluation of the RES uptake of the CHA-liposome vehicle and the PEG-liposome vehicle containing the radiolabeled conjugate, determined by the ratio of the [³H] biodistribution dose remaining in the total of the liver together with the spleen, divided by the dose in the blood, or (L+S)/B.

It has been established that cHyp covalently attached to the carrier poly(PEG-Lys) results in an enhanced and prolonged duration of effect, as demonstrated in both in vitro and in vivo models; see Poiani et al., Bioconjugate Chemistry, 1994, 5(6):621–630. However, attachment of cHyp by way of an amide linkage to the poly(PEG-Lys) carrier as a last step proceeds with a significant degree of variability, on the order of 14 to 65%; Poiani, G. J., et at., supra. Based on the high bioactivity of this amide conjugate, both in vitro and in vivo, towards collagen inhibition, it was a goal of the present invention to devise a synthetic rationale which would obtain maximum, i.e., consistent cHyp loading efficiency. In order to achieve this goal, it was necessary to abandon the nonspecific approach previously employed, in which the PEG-Lys carrier system provided for drug conjugation only by means of last step attachment of therapeutic agents. Instead, the process was totally rearranged to allow for the specific tailoring of appropriate drug conjugates prior to their incorporation into the carrier by polymerization. This was accomplished by the use of the Lys-cHyp dipeptide as the drug-containing chain extender (FIG. 10 and Scheme 1: Step a). The polymerization of the BSC-PEG through the free primary α- and δ-amines of the Lys component of the dipeptide was carried out using a known reaction. The result was polymeric conjugates with 100% drug incorporation in relatively high yields (FIG. 11 and Scheme 1: Step b). The Lys-cHyp dipeptide synthesis proceeded with a purified overall yield of 50%, and yields from copolymerization with BSC-PEG were consistently >98%.

Conjugate Hydrolytic Stability

It has been established that the poly(PEG-Lys) backbone remains intact over at least a 48 h period in human plasma; see Nathan et al., *Bioconjugate Chem.*, 1993, 4:54–62. However, at that time, hydrolytic and serum stability studies were not conducted on the conjugate of polymer backbone and attached drug.

The polymeric conjugate consists of two distinctly different parts: (a) the polymeric backbone [poly(PEG-Lys)]; and (b) the pendent chain which consists of the drug molecule and its linking bond (cHyp). In order to study the stability of the polymeric conjugate, a dual radio-labeled polymeric conjugate was prepared containing [$^{14}$C]-labeled lysine in the backbone, and [$^3$H]-labeled cis-4-hydroxyproline in the pendent chain. This experimental design made it possible to evaluate the stability of the polymer backbone by conventional GPC analysis while measuring the release of drug from the backbone by monitoring the [$^3$H] to [$^{14}$C] ratio in the polymeric conjugate. In order to determine the hydrolytic stability of the polymeric conjugate over a wide range of conditions, the radio-labeled polymeric conjugate was incubated in buffered solutions ranging in pH from highly acidic to highly basic. The test solutions were maintained at a constant temperature of 25° C. The hydrolytic stability of the polymeric conjugate was monitored over a six day period. The stability of the bonds present in the polymeric conjugate (ether, amide and urethane) was evaluated by incubation of the dual-labeled polymeric conjugate at the specified pH. Aliquot removal at specified time intervals, followed by GPC analysis with fractionation, permitted the quantitative monitoring of both carrier stability (molecular weight profile) and drug release (determination of [$^3$H]/[$^{14}$C] ratio by scintillation counting), as is shown in FIG. 12. In the pH range from 0 to 12, no change in either molecular weight, polydispersity or the [$^3$H] to [$^{14}$C] ratio could be detected throughout the test period. Massive backbone degradation was observed only at pH 14, but this was accompanied by relatively no change in the [$^3$H]/[$^{14}$C] ratios, indicating high amide stability. Examination of the GPC traces over the six day period for pH 14 revealed cleavage events giving rise to discernible and discrete traces that are multiples of approximately 2,000 g/mol, i.e., the molecular weight of the PEG spacer unit. These results are unequivocal evidence that at ambient temperatures, the polymer backbone as well as the linking amide bond between cHyp and the polymer backbone are unaffected by acidic, neutral, or weakly basic storage conditions over a period of at least six days.

It was further observed that cleavage of [$^3$H]cHyp from the carrier did not occur to any appreciable extent over a six day incubation in FCS at 37° C. Polymer backbone stability was completely maintained, as previously demonstrated; Nathan et al., supra. From these results one may imply that the polymeric conjugate is stable in a cell-free serum environment and that digestion/release of the cHyp is probably mediated by some mechanism within the cellular tissue. One may further imply that the hydrolytic events which drive this system are enzymatically mediated, perhaps by proteolytic enzymes.

Organ Distribution and In Vivo Stability of Radiolabeled Polymeric Conjugate Delivered by Liposomal Vehicle Since uptake and retention of liposomes in tissues is an important determinant of bioactivity, a comparison was made between the organ distribution and retention of two types of liposomes, using previously described methods; Poiani et al., *Circ. Rcs.*, 1992, 70:912–922. Radioactivity in lung, liver, spleen and blood were measured at 6 hr and 7 days (Table 6). These times were previously found to show peak uptake (6 hr) and prolonged retention (7 days); Poiani et al., supra. The results, expressed as a % of the total amount of injected [$^3$H] per gram of tissue or total blood volume, were compared between the PEG-liposome and CHA-liposome compositions. The results 6 hrs after injection showed that most of the [$^3$H]cHyp for both liposomes had become localized in the spleen and blood, and that the lung had the least amount of radioactivity. PEG-liposomes have been observed to be splenotropic, which probably explains the high initial uptake observed. Activity in all organs had decreased at the end of 7 days.

Importantly, the amount of [$^3$H]cHyp in the lung with the CHA-liposomes was 11% at 6 hr and 5% at 7 days, while the radioactivity for the PEG-liposomes was 7.5% at 6 hr and 2.5% at 7 days, or half the amount of the CHA-liposomes at 7 days (p<0.05). The trend toward greater [$^3$H]cHyp retention in the lungs by CHA-liposomes than by PEG-liposomes may be explained in terms of the active targeting of the liposomes within the lung to the cells thereof. The primary difference between the two types of liposomes is the polysaccharide coating of the CHA-liposomes, which thus raises the possibility that it is being recognized by a saccharide-specific receptor. PEG-conjugated liposomes, on the other hand, enable one to achieve passive targeting to non-reticuloendothelial cell organs by inhibiting non-specific clearance and opsonization of liposomes by the reticuloendothelial cell system; Allen et al., *Biochem. Biophys. Acta*, 1991, 1066:29–36; Gabizon et al., *Proc. Natl. Acad. Sci. USA*, 1988, 85:6964–6973; Kilibanov et al., *FEBS Lett.*, 1990, 268:235–237. Attachment of polysaccharides such as CHA onto the surface of liposomes provides a cytophilic ligand for active targeting within the lung to the cells thereof; Sato and Sunamota; *Prog. Lipid Res.*, 1992, 31:345–372; Takcada et al., *Biochim. Biophys. Acta*, 1984, 802:237–244; Mauk et al., *Proc. Natl. Acad. Sci. USA*, 1980, 77:4430–4434; said cells having saccharide-specific surface receptors; Sharon and Lis, *FASEB J.*, 1990, 4:3198–3208. There have been no prior studies of the uptake of polysaccharide coated liposomes by pulmonary artery endothelial cells.

Delivery of the antifibrotic drug cHyp can be determined by the percentage of the [$^3$H]cHyp dose retained (Table 6) and the [$^3$H]/[$^{14}$C] ratio (Table 7) after liposomal delivery of the dual-labeled conjugate to selected organs. [$^3$H]/[$^{14}$C] ratios in the lungs are higher at 6 hrs than for the pre-incubation ratio for both liposome types. At the end of 7 days, the [$^3$H]/[$^{14}$C] ratio is higher for the PEG-liposome by almost a factor of two, even though the concentration of [$^3$H]cHyp is twice as high using the CHA-liposome. The inference which one can make is that [$^3$H]cHyp released from the polymeric conjugate is more prevalent in lung tissue as a result of delivery in PEG-liposomes, and that the CHA coating imparts a longer duration of stability to the polymeric conjugate, which may be as a result of decreased leakage of the polymeric conjugate. Coating liposomes with polysaccharides is known to decrease leakage of water soluble agents therefrom, and to increase the resistance of the liposomes to enzymatic lysis, compared to uncoated liposomes; Sunamoto et al., *Polymers in Medicine*, Chiellini and Giusti, eds., Plenum Press, 1983, 157–168. A lower [$^3$H]/[$^{14}$C] ratio and higher [$^3$H]cHyp concentration in the lung tissue (at similar encapsulation efficiencies for both liposomes types) implies prolonged release and the corresponding strong possibility of achieving a sustained drug concentration over a prolonged period.

The conjugate appears to be relatively stable in both the liver and spleen for both liposomal types for at least 6 hrs, and essentially for the PEG-liposome at 7 days. This conjugate stability may actually be due to liposomal stability within these organs, in view of the fact that a relatively high percentage of the initial dose remained.

For the lung, the [$^3$H]/[$^{14}$C] ratio at 7 days was observed to be higher by approximately 1.8× for the PEG-liposome and 1.3× for the CHA-liposome, compared to the ratio level at 6 h. This moderate increase in the [$^3$H]/[$^{14}$C] ratios within the lung is offset by the relatively higher [$^3$H]/[$^{14}$C] ratios observed in the blood. One explanation for this result takes into consideration the fact that "defective" collagen, i.e., that containing cHyp, is being digested intracellularly and released into the bloodstream at some given rate. Such free [$^3$H]cHyp would thus be responsible for the higher observed [$^3$H]/[$^{14}$C] ratio. Another explanation is that the polymeric conjugate is not stable within the environment of the circulating blood. However, this approach fails to take into consideration the fact that where the circulating liposomes are intact, there is necessary a very minimal amount of contact between the contents of the liposomes and the blood.

Increased blood circulation times and slower removal by the reticuloendothelial system (RES) of the CHA-liposomes as compared to the PEG-liposomes can be inferred by evaluation of the [$^3$H]cHyp biodistribution levels in both the liver and spleen taken together, compared to the levels in the blood [(L+S)/B]. This comparison is useful for determining the relative rate of RES clearance; Papahadjopoulos et al., *Proc. Natl. Acad. Sci. USA,* 1991, 88:11460–11464; Woodle et al., *Biochim. Biophys. Acta,* 1992, 1105:193–200; Woodle et al., *Bioconjugate Chem.,* 1994, 5(6):493–496. As is shown in FIG. 4, RES uptake at 6 hrs for both liposome types is relatively low. However, after 7 days, the CHA-liposome remains close to the original low level, while the PEG-liposome has increased by a factor of nine as compared to the level at the 6 hr time point. Taking into account the low RES clearance and higher [$^3$H]cHyp content in the blood with the CHA-liposome, the possibility of a lung capillary embolism as the causitive mechanism can be excluded.

This invention may be embodied in other forms or carried out in other ways than those described above without departing from the spirit or essential characteristics thereof. The present disclosure is therefore to be considered in all respects as merely illustrative and not restrictive, the scope of the invention being defined by the appended claims, and all changes which come within the meaning and range of equivalency are intended to be embraced therein.

What is claimed is:

1. A copolymer conjugate antifibrotic composition comprising:
   (1) a dipeptide consisting of
      (a) an L-proline or derivative antifibrotic agent selected from the group consisting of 3,4-dihydro-L-proline, laevo and cis isomers of compounds of the general structural formula:

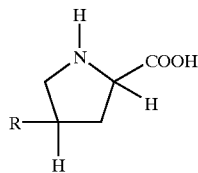

wherein R is selected from OH, Cl, F, NH$_2$, SH, SCH$_3$, ONO$_2$, OSO$_2$, OSO$_3$,H, H$_2$PO$_4$, or COOH, and combinations thereof and pharmaceutically acceptable salts thereof; and
      (b) L-lysine to which said L-proline or derivative antifibrotic agent is covalently bound to form each dipeptide; and
   (2) a polymer to which said dipeptide is covalently bound to form a copolymer conjugate, said polymer selected from the group consisting of ethyl glycol, propylene glycol, butylene glycol, isobutylene glycol,
      wherein said L-proline or derivative antifibrotic agent is present in said copolymer conjugate in excess of 98% of the maximum capacity of said copolymer conjugate for said antifibrotic agent.

2. A composition according to claim 1 wherein said L-proline or derivative antifibrotic agent is cis-4-hydroxyproline, and said polymer is poly(ethylene glycol) having a weight average molecular weight of from about 500 to about 15,000.

3. A copolymer conjugate antifibrotic composition prepared by the process comprising:
   (1) covalently binding L-proline or derivative antifibrotic agent selected from the group consisting essentially of 3,4-dehydro-L-proline, laevo and cis isomers of compounds of the general structural formula:

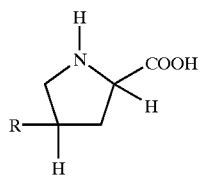

wherein R is selected from OH, Cl, F, NH$_2$, SH, SCH$_3$, OCH$_3$, ONO$_2$, OSO$_2$, OSO$_3$,H, H$_2$PO$_4$, COOH and combinations thereof; and pharmaceutically acceptable salts thereof; to
   (2) L-lysine to form at least one dipeptide and thereafter,
   (3) covalently binding each said dipeptide to said one or more polymers to form said copolymer conjugate;
      wherein said formation of said copolymer conjugate proceeds to give in excess of a 97% yield.

4. A composition according to claim 3 wherein said L-proline or derivative antifibrotic agent is cis-4-hydroxyproline, and said polymer is poly(ethylene glycol) having a weight average molecular weight of from about 500 to about 15,000.

5. A copolymer conjugate antifibrotic composition according to claim 3 wherein the N-hydroxysuccinimide ester of said L-lysine is used in said coupling reaction.

* * * * *

UNITED STATES PATENT AND TRADEMARK OFFICE
CERTIFICATE OF CORRECTION

PATENT NO. : 6,517,824 B1
DATED : February 11, 2003
INVENTOR(S) : Joachim Kohn et al.

It is certified that error appears in the above-identified patent and that said Letters Patent is hereby corrected as shown below:

<u>Column 1,</u>
Line 25, before "FIELD OF THE INVENTION," insert the following paragraph:
-- STATEMENT REGARDING FEDERALLY SPONSORED RESEARCH OR DEVELOPMENT
  This invention was made with government support under Grant No. HL24264 awarded by National Institutes of Health. The Government has certain rights in the invention. --

Signed and Sealed this

Twenty-fourth Day of June, 2003

JAMES E. ROGAN
*Director of the United States Patent and Trademark Office*